Figure 1:
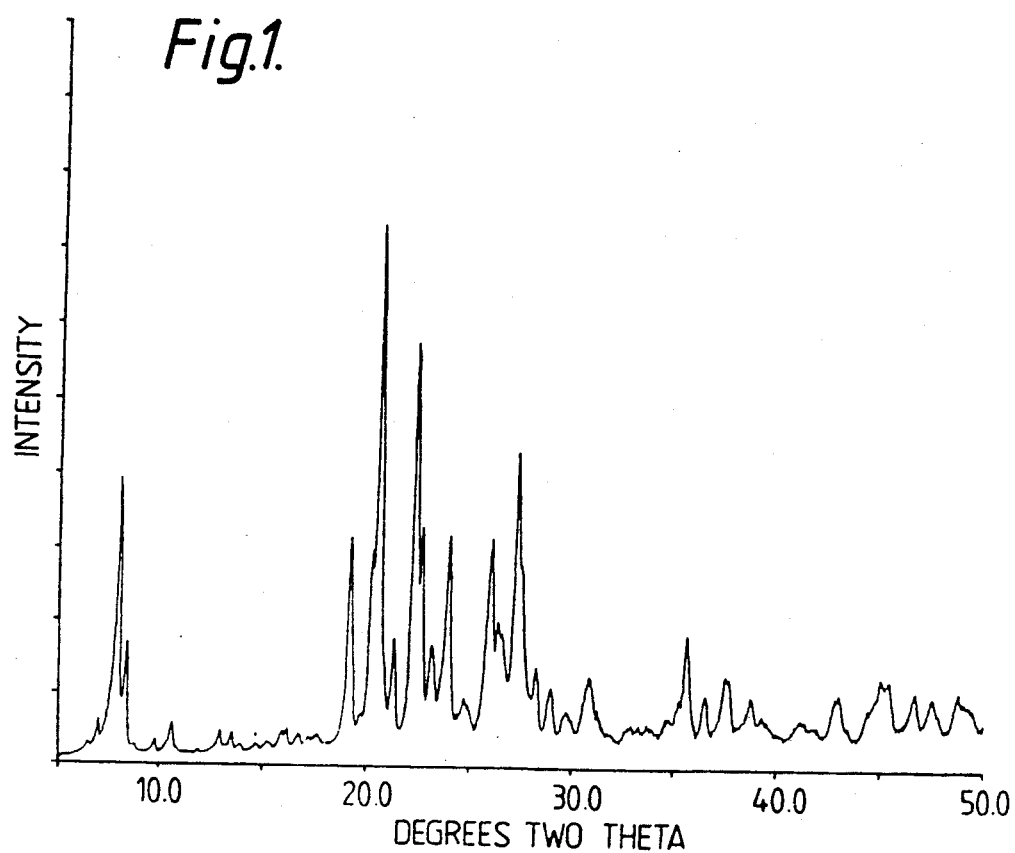

United States Patent [19]

Casci et al.

[11] Patent Number: 5,041,402
[45] Date of Patent: Aug. 20, 1991

[54] CATALYTIC REACTIONS USING ZEOLITES

[75] Inventors: John L. Casci; Ivan J. S. Lake, both of Cleveland; Timothy R. Maberly, Eaglescliffe, all of United Kingdom

[73] Assignee: Imperial Chemical Industries PLC, London, England

[21] Appl. No.: 453,305

[22] Filed: Dec. 22, 1989

[30] Foreign Application Priority Data

Dec. 22, 1988 [GB] United Kingdom ................ 8829923

[51] Int. Cl.$^5$ ............................................. B01J 29/28
[52] U.S. Cl. ......................................... 502/67; 502/60
[58] Field of Search ............................. 502/60, 62, 67

[56] References Cited

U.S. PATENT DOCUMENTS

| | | | |
|---|---|---|---|
| 4,634,686 | 1/1987 | Desmond et al. | 502/60 |
| 4,757,041 | 7/1988 | Oleck et al. | 502/67 |

FOREIGN PATENT DOCUMENTS

| | | | |
|---|---|---|---|
| 55045 | 6/1982 | European Pat. Off. | 502/60 |
| 1337752 | 11/1973 | United Kingdom . | |
| 1521101 | 8/1978 | United Kingdom . | |

Primary Examiner—Carl F. Dees
Attorney, Agent, or Firm—Cushman, Darby & Cushman

[57] ABSTRACT

A catalyst comprising a novel zeolite NU-87, is useful in a wide variety of hydrocarbon conversion reactions including isomerisation, transalkylation and alkylation.

5 Claims, 4 Drawing Sheets

CATALYTIC REACTIONS USING ZEOLITES

The present invention relates to a novel zeolite hereinafter referred to as zeolite NU-87, to a method of making it, and to processes using it as a catalyst.

According to the present invention we provide a catalyst and processes catalysed thereby characterised by a zeolite, referred to hereinafter as NU-87, having a chemical composition expressed on an anhydrous basis, in terms of the mole ratios of oxides, by the formula:

100 $XO_2$: equal to or less than 10 $Y_2O_3$: equal to or less than 20 $R_{2/n}O$ where
  R is one or more cations of valency n,
  X is silicon and/or germanium,
  Y is one or more of aluminium, iron, gallium, boron, titanium, vanadium, zirconium, molybdenum, arsenic, antimony, chromium and manganese and having, in its as-prepared form, an X-ray diffraction pattern including the lines shown in Table 1.

The zeolite NU-87 may be present in the catalyst in its hydrogen form, designated H-NU-87, produced by calcination and/or ion exchange as described herein. Zeolite H-NU-87 has an X-ray diffraction pattern including the lines shown in Table 2.

TABLE 1

Zeolite NU-87 as-prepared

| d(Angstroms) | Relative Intensity[d] |
|---|---|
| 12.52 ± 0.15 | w |
| 11.06 ± 0.15 | s |
| 10.50 ± 0.15 | m |
| 8.31 ± 0.15 | w |
| 6.81 ± 0.12 | w |
| 4.62 ± 0.10 | m-s |
| [a]4.39 (Sh) ± 0.10 | m-s |
| 4.31 ± 0.10 | vs |
| 4.16 ± 0.10 | m |
| 3.98 ± 0.08 | s-vs |
| [b]3.92 (Sh) ± 0.08 | s |
| 3.83 ± 0.08 | w-m |
| 3.70 ± 0.07 | m-s |
| 3.61 ± 0.07 | w |
| 3.41 ± 0.07 | m-s |
| [c]3.37 (Sh) ± 0.07 | m |
| 3.26 ± 0.06 | s-vs |
| 3.15 ± 0.06 | w |
| 3.08 ± 0.06 | w |
| 2.89 ± 0.05 | w-m |
| 2.52 ± 0.04 | w-m |

(Sh) denotes that the peak occurs as a shoulder on a more intense peak
[a]occurs on the low angle side of the peak at about 4.31A
[b]occurs on the high angle side of the peak at about 3.98A
[c]occurs on the high angle side of the peak at about 3.41A
[d]Based on a relative intensity scale in which the strongest line in the X-ray pattern is assigned a value of 100:
weak (w) is less than 20
medium (m) is between 20 and 40
strong (s) is greater than 40 but less than 60
very strong (vs) is greater than 60.

TABLE 2

ZEOLITE NU-87 IN ITS HYDROGEN FORM, H-NU-87

| d(Angstroms) | Relative Intensity[d] |
|---|---|
| 12.44 ± 0.15 | w |
| 11.12 ± 0.15 | vs |
| 10.52 ± 0.15 | m-s |
| 8.33 ± 0.15 | w |
| 6.81 ± 0.12 | w-m |
| 4.60 ± 0.10 | s-vs |
| [a]4.39 (Sh) ± 0.10 | m-s |
| 4.32 ± 0.10 | vs |
| 4.17 ± 0.10 | m |
| 3.98 ± 0.08 | vs |
| [b]3.91 (Sh) ± 0.08 | s |
| 3.84 ± 0.08 | w |
| 3.73 ± 0.07 | m-s |
| 3.60 ± 0.07 | w |
| 3.41 ± 0.07 | s |
| [c]3.37 (Sh) doublet ± 0.07 | m-s |
| 3.34 | |
| 3.26 ± 0.06 | vs |
| 3.16 ± 0.06 | w-m |
| 3.08 ± 0.06 | w-m |
| 2.90 ± 0.05 | w-m |
| 2.51 ± 0.04 | m |

(Sh) denotes that the peak occurs as a shoulder on a more intense peak
[a]occurs on the low angle side of the peak at about 4.32A
[b]occurs on the high angle side of the peak at about 3.98A
[c]occurs on the high angle side of the peak at about 3.41A
[d]Based on a relative intensity scale in which the strongest line in the X-ray pattern is assigned a value of 100:
weak (w) is less than 20
medium (m) is between 20 and 40
strong (s) is greater than 40 but less than 60
very strong (vs) is greater than 60.

In the diffractograms from which X-ray data are obtained some, or all, of the shoulders and doublets shown in Tables 1 and 2 may not be resolved from the stronger peaks with which they are associated. This may occur for poorly crystalline samples or in samples in which the crystals are sufficiently small to result in significant X-ray broadening. It may also occur if the equipment, or conditions, used to obtain the pattern differ from those used herein.

The X-ray powder diffraction data provided herein were obtained with a Philips APD 1700 automated X-ray diffraction system using Cu K-alpha radiation from a long fine focus X-ray tube operating at 40 KV and 50 mA. The radiation was monochromatised by a curved graphite crystal adjacent to the detector. An automatic theta-compensating divergence slit was used with a 0.1 mm receiving slit. Step scanned data were collected between 1 and 60 degrees two-theta. The collected data were analysed in a DEC (Digital Equipment Corporation) Micro PDP -11/73 computer with Philips PW 1867/87 version 3.0 software.

It is believed that NU-87 has a new framework structure or topology which is characterised by its X-ray diffraction pattern. NU-87 in its as-prepared and hydrogen forms has substantially the X-ray data given in Tables 1 and 2 respectively and is thereby distinguished from known zeolites. In particular it is distinguished from zeolite EU-1, as described in European Patent 42226, since the X-ray diffraction pattern for EU-1 does not contain an X-ray line at about 12.5 A. Furthermore the X-ray diffraction pattern for EU-1 contains an X-ray line at about 10.1 A which line is absent from the X-ray diffraction patterns of NU-87.

Within the above definition of chemical composition the number of moles of $Y_2O_3$ per 100 moles of $XO_2$ is typically in the range 0.1 to 10 for example 0.2 to 7.5 and zeolite NU-87 appears to be most readily formed in a state of high purity when the number of moles of $Y_2O_3$ per 100 moles of $XO_2$ is in the range 0.4 to 5.

This definition includes as-prepared NU-87 and also forms of it resulting from dehydration and/or calcination and/or ion exchange. The expression "as-prepared" means the product of synthesis and washing with or without drying or dehydration. In its as-prepared form NU-87 may include M, an alkali-metal cation, especially sodium and/or ammonium and, when prepared for example from alkylated nitrogen compounds, may include nitrogen-containing organic cations as described below or degradation products thereof or precursors thereof. Such nitrogen-containing organic cations are hereinafter referred to as Q.

Thus zeolite NU-87, as-prepared, has the following molar composition, expressed on an anhydrous basis:

100 $XO_2$: less than or equal to 10 $Y_2O_3$: less than or equal to 10 Q: less than or equal to 10 $M_2O$ where Q is the nitrogen-containing organic cation referred to above and M is the alkali metal and/or ammonium cation.

The compositions for NU-87 above are given on an anhydrous basis, although as-prepared NU-87 and activated forms of NU-87 resulting from calcination and/or ion exchange may contain water. The molar $H_2O$ content of such forms, including as-prepared NU-87, depends on the conditions under which it has been dried and stored after synthesis or activation. The range of molar quantities of contained water is typically between 0 and 100 per 100 $XO_2$.

Calcined forms of zeolite NU-87, include no nitrogen-containing organic compound or less than the as-prepared form, since the organic material is burned out in the presence of air, leaving hydrogen ion as the other cation.

Among the ion-exchanged forms of zeolite NU-87 the ammonium ($NH_4^+$) form is of importance since it can be readily converted to the hydrogen form by calcination. The hydrogen form and forms containing metals introduced by ion exchange are described below. Under some circumstances exposure of the zeolite of the invention to acid can result in partial or complete removal of a framework element such as aluminium as well as the generation of the hydrogen form. This can provide a means of altering the composition of the zeolite material after it has been synthesised.

Zeolite NU-87 may also be characterised by its sorptive capacity for molecules of various sizes. Table 3 contains sorption results which were obtained on the hydrogen form of zeolite NU-87, the product from example 6.

The data were obtained using a McBain-Bakr spring balance for water and methanol and a CI Robal Microbalance for all other sorbates. Samples were outgassed at 300° C., overnight, before measurements were made. Results are presented as % (w/w) uptake at relative pressures (P/Po) where Po is the saturated vapour pressure. The figures for apparent voidage filled were calculated assuming that the liquids maintain their normal densities at the sorption temperature.

TABLE 3

Sorption data for H-NU-87

| Sorbate | Adsorption Temperature [°C.] | Relative Pressure | Uptake [% (w/w)] | Apparent Voidage[1] filled [$cm^3g^{-1}$] | Kinetic Diameter[2] nm |
|---|---|---|---|---|---|
| Water | 25.4 | 0.07 | 5.4 | 0.054 | 0.265 |
|  |  | 0.28 | 8.3 | 0.083 |  |
|  |  | 0.46 | 10.0 | 0.100 |  |
| Methanol | 25.2 | 0.10 | 10.3 | 0.130 | 0.380 |
|  |  | 0.29 | 11.6 | 0.147 |  |
|  |  | 0.50 | 12.3 | 0.156 |  |
| n-Hexane | 26.7 | 0.13 | 11.0 | 0.167 | 0.430 |
|  |  | 0.31 | 11.5 | 0.175 |  |
|  |  | 0.52 | 12.0 | 0.182 |  |
| Toluene | 26.7 | 0.11 | 12.3 | 0.142 | 0.585 |
|  |  | 0.32 | 13.2 | 0.152 |  |
|  |  | 0.48 | 13.6 | 0.157 |  |
| Cyclohexane | 26.7 | 0.12 | 11.6 | 0.149 | 0.600 |
|  |  | 0.37 | 12.2 | 0.157 |  |
|  |  | 0.49 | 12.5 | 0.160 |  |
| Neopentane (2.2-dimethyl propane) | 0.0 | 0.11 | 3.29 | 0.05 | 0.620 |
|  |  | 0.32 | 5.55 | 0.09 |  |
|  |  | 0.54 | 8.54 | 0.14 |  |

[1] The apparent voidage filled was calculated assuming the liquids maintain their normal densities at the adsorption temperature
[2] Kinetic diameters are taken from "Zeolite Molecular Sieves". D W Breck, J Wiley and Sons, 1976 p636. The value for methanol was assumed to be the same as for methane, n-hexane the same as n-butane and toluene the same as benzene.
[3] The uptake is grams of sorbate per 100 grams of anhydrous zeolite.

The kinetic diameters given in the extreme right hand column of Table 3 were taken from "Zeolite Molecular Sieves" D W Breck, J Wiley and Sons, 1976 (p636), with the value for methanol assumed to be the same as for methane, the value for n-hexane to be the same as for n-butane and for value for toluene to be the same as for benzene.

The results show that NU-87 has significant capacity for various sorbates at low partial pressures. The low uptake for water, compared with methanol, n-hexane, toluene and cyclohexane, indicates that NU-87 has significant hydrophobic character. The results in Table 3 indicate that zeolite NU-87 shows a molecular sieving effect with respect to neopentane since much lower uptakes were observed compared with the other hydrocarbon sorbates at similar relative pressures. In addition the time required to reach equilibrium was much longer than for the other hydrocarbon sorbates. These results indicate that NU-87 has a window size close to 0.62 nanometers.

The invention also provides a method for the preparation of zeolite NU-87 which comprises reacting an aqueous mixture comprising a source of at least one oxide $XO_2$, optionally a source of at least one oxide $Y_2O_3$, optionally a source of at least one oxide $M_2O$ and at least one nitrogen-containing organic cation Q, or precursors thereof, the mixture preferably having the molar composition:

$XO_2/Y_2O_3$ at least 10, more preferably 10 to 500, most preferably 20 to 200

$(R_{1/n})OH/XO_2$ is 0.01 to 2, more preferably 0.05 to 1, most preferably 0.10 to 0.50

$H_2O/XO_2$ is 1 to 500, more preferably 5 to 250, most preferably 25 to 75

$Q/XO_2$ is 0.005 to 1, more preferably 0.02 to 1, most preferably 0.05 to 0.5

$L_pZ/XO_2$ is 0 to 5, more preferably 0 to 1, most preferably 0 to 0.25 where X is silicon and/or germanium, Y is one or more of aluminium, iron, boron, titanium, vanadium, zirconium, molybdenum, arsenic, antimony, gallium, chromium, manganese, R is a cation of valency n which can include M, (an alkali metal cation and/or ammonium), and/or Q, (a nitrogen-containing organic cation, or a precursor thereof). In some circumstances it may be an advantage to add a salt $L_pZ$ where Z is an anion of valency p and L is an alkali metal or ammonium ion which may be the same as M or a mixture of M and another alkali metal or an ammonium ion necessary to balance the anion Z. Z may comprise an acid radical added for example as a salt of L or as a salt of aluminium. Examples of Z may include strong acid radicals such as bromide, chloride, iodide, sulphate, phosphate or nitrate or weak acid radicals such as organic acid radicals, for example citrate or acetate. While $L_pZ$ is not essential, it may accelerate the crystallisation of zeolite NU-87 from the reaction mixture and may also affect the crystal size and shape of NU-87. The reaction is continued until it contains a major proportion i.e. at least 50.5% of zeolite NU-87.

Many zeolites have been prepared using nitrogen-containing organic cations or degradation products thereof or precursors thereof and in particular, polymethylene alpha omega-diammonium cations having the formula:

$$[(R_1R_2R_3)N(CH_2)_mN(R_4R_5R_6)]^{2+}$$

where $R_1$ to $R_6$, which may be the same or different, can be hydrogen, alkyl or hydroxyalkyl groups containing from 1 to 8 carbon atoms, and up to five of the groups can be hydrogen, and m is in the range 3 to 14. For example zeolite EU-1 (EP 42226), zeolite EU-2 (GB 2 077 709) and zeolite ZSM-23 (EP 125 078, GB 2 202 838) have been prepared using such templates. The use of these templates in the preparation of zeolites and molecular sieves has also been described in the PhD thesis of J L Casci entitled "The Use of Organic Cations in Zeolite Synthesis" (1982) The University of Edinburgh, and in the following papers: G W Dodwell, R P Denkewicz and L B Sand "Zeolites", 1985, vol 5, page 153 and J L Casci Proc. VII Int. Zeolite Conf., Elsevier, 1986, page 215.

In the method according to the present invention Q is preferably a polymethylene alpha, omega-diammonium cation having the formula:

$$[(R_1R_2R_3)N(CH_2)_mN(R_4R_5R_6)]^{2+}$$

or an amine degradation product thereof, or a precursor thereof where $R_1, R_2, R_3, R_4, R_5$ and $R_6$ may be the same or different and are $C_1$ to $C_3$ alkyl and m is in the range of 7 to 14

Q is more preferably $$[(CH_3)_3N(CH_2)_mN(CH_3)_3]^{2+}$$

where m is in the range 8 to 12, and is most preferably $$[(CH_3)_3N(CH_2)_{10}N(CH_3)_3]^{2+}$$

and M and/or Q can be added as hydroxides or salts of inorganic acids provided the $(R_{1/n})OH/XO_2$ ratio is fulfilled.

Suitable precursors of the nitrogen-containing organic cation Q include the parent diamine with a suitable alkyl halide or the parent dihaloalkane with a suitable trialkylamine. Such materials can be used as simple mixtures or they can be pre-heated together in the reaction vessel, preferably in solution, prior to the addition of the other reactants required for the synthesis of zeolite NU-87.

The preferred cation M is an alkali metal especially sodium, the preferred $XO_2$ is silica ($SiO_2$) and the preferred oxide $Y_2O_3$ is alumina ($Al_2O_3$).

The silica source can be any of those commonly considered for use in synthesising zeolites, for example powdered solid silica, silicic acid, colloidal silica or dissolved silica. Among the powdered silicas usable are precipitated silicas, especially those made by precipitation from an alkali metal silicate solution, such as the type known as "KS 300" made by AKZO, and similar products, aerosil silicas, fumed silicas e.g. "CAB-O-SIL" and silica gels suitably in grades for use in reinforcing pigments for rubber and silicone rubber. Colloidal silicas of various particle sizes may be used, for example 10–15 or 40–50 microns, as sold under the Registered Trade Marks "LUDOX", "NALCOAG" and "SYTON". The usable dissolved silicas include commercially available waterglass silicates containing 0.5 to 6.0, especially 2.0 to 4.0 mols of $SiO_2$ per mol of alkali metal oxide, "active" alkali metal silicates as defined in UK Patent 1193254, and silicates made by dissolving silica in alkali metal hydroxide or quaternary ammonium hydroxide or a mixture thereof.

The optional alumina source is most conveniently sodium aluminate, or aluminium, an aluminium salt, for example the chloride, nitrate or sulphate, an aluminium alkoxide or alumina itself, which should preferably be in a hydrated or hydratable form such as colloidal alumina, pseudoboehmite, boehmite, gamma alumina or the alpha or beta trihydrate. Mixtures of the above can be used.

Optionally all or some of the alumina and silica source may be added in the form of an aluminosilicate.

The reaction mixture is usually reacted under autogenous pressure, optionally with added gas, e.g. nitrogen, at a temperature between 85° C. and 250° C., preferably 120° C. and 200° C., until crystals of zeolite NU-87 form, which can be from 1 hour to many months depending on the reactant composition and the operating temperature. Agitation is optional, but is preferable since it reduces the reaction time and can improve product purity.

The use of seed material can be advantageous in decreasing the time to nucleation and/or overall crystallisation time. It may also be an advantage in encouraging the formation of NU-87 at the expense of an impurity phase. Such seed materials include zeolites, especially crystals of zeolite NU-87. The seed crystals are usually added in an amount of between 0.01 and 10% of the weight of silica used in the reaction mixture. The use of a seed is particularly desirable when the nitrogen-containing organic cation is a polymethylene alpha, omega-diammonium cation with seven, eight or nine methylene groups i.e. m is 7, 8 or 9.

At the end of the reaction, the solid phase is collected in a filter and washed, and is then ready for further steps such as drying, dehydration and ion exchange.

If the product of the reaction contains alkali metal ions, these have to be at least partly removed in order to prepare the hydrogen form of NU-87 and this can be done by ion-exchange with an acid, especially a mineral acid such as hydrochloric acid or by way of the ammonium compound, made by ion exchange with a solution of an ammonium salt such as ammonium chloride. Ion exchange may be carried out by slurrying once or several times with the ion exchange solution. The zeolite is usually calcined before ion exchange to remove any occluded organic matter since this usually facilitates ion exchange.

In general, the cation(s) of zeolite NU-87 can be replaced by any cation(s) of metals, and particularly those in groups 1A, 1B, IIA, IIB, IIIA and IIIB (including rare earths) VIII (including noble metals) other transition metals and by tin, lead and bismuth. (The Periodic Table is as in "Abridgements of Specifications" published by the UK Patent Office). Exchange is normally carried out using a solution containing a salt of the appropriate cation.

Methods for preparing NU-87 are illustrated by the following Examples.

EXAMPLE 1

Preparation of NU-87

A reaction mixture of molar composition:

$60\ SiO_2—1.333\ Al_2O_3—10\ Na_2O—7.5\ DecBr_2—3500\ H_2O$ was prepared from:
- 120.2 g "SYTON" X30 (Monsanto: 30% silica sol)
- 6.206 g "SOAL" 235 (Kaiser Chemicals: molar composition 1.59 $Na_2O$ —1.0 $Al_2O_3$—14.7 $H_2O$.
- 6.30 g Sodium Hydroxide (Analar)
- 31.4 g $DecBr_2$
- 541.5 g Water (deionised)

where $DecBr_2$ is Decamethonium Bromide:

$[(CH_3)_3N(CH_2)_{10}N(CH_3)_3]Br_2$

The molar composition given above does not include sodium present in the "SYTON".

The mixture was prepared as follows:
- A—solution containing the sodium hydroxide and "SOAL" 235 in 200 g of water
- B—solution containing the $DecBr_2$ in 200 g of water
- C—141.5 g of water Solution A was added to the "SYTON" X30, with stirring, over a 30 second period. Mixing was continued for 5 minutes then solution B was added, with stirring, over a 30 second period. Finally, the remaining water, C, was added over a 30 second period. The resulting gel was mixed for a further 5 minutes before being transferred to a 1 liter stainless steel autoclave.

The mixture was reacted at 180° C., with stirring at 300 rpm using a pitched-paddle type impeller.

About 9 days into the reaction the heating and stirring were stopped for about 2.5 hours before the preparation was restarted.

After a total of 406 hours, at reaction temperature, the preparation was crash cooled to ambient and the product discharged, filtered, washed with deionised water and dried at 110° C.

Analysis for Si, Al and Na by atomic adsorption spectroscopy (AAS) gave the following molar composition:

$37.6\ SiO_2—1.0\ Al_2O_3—0.14\ Na_2O$

Analysis by X-ray powder diffraction showed this as-prepared material to be highly crystalline sample of NU-87 with the pattern shown in Table 4 and FIG. 1.

EXAMPLE 2

Preparation of Hydrogen NU-87

A portion of the material from Example 1 was calcined, in air, at 450° C. for 24 hours followed by 16 hours at 550° C. The material was then ion exchanged for 4 hours with a 1 molar solution of ammonium chloride, at room temperature, using 10 ml of solution per gram of zeolite. After two such exchanges the resulting $NH_4$-NU-87 was then calcined at 550° C. for 16 hours to generate the hydrogen form, that is, H-NU-87.

Analysis by AAS for Si, Al and Na gave the following molar composition:

$36.8\ SiO_2—1.0\ Al_2O_3—less\ than\ 0.001 Na_2O$

Figure 2:
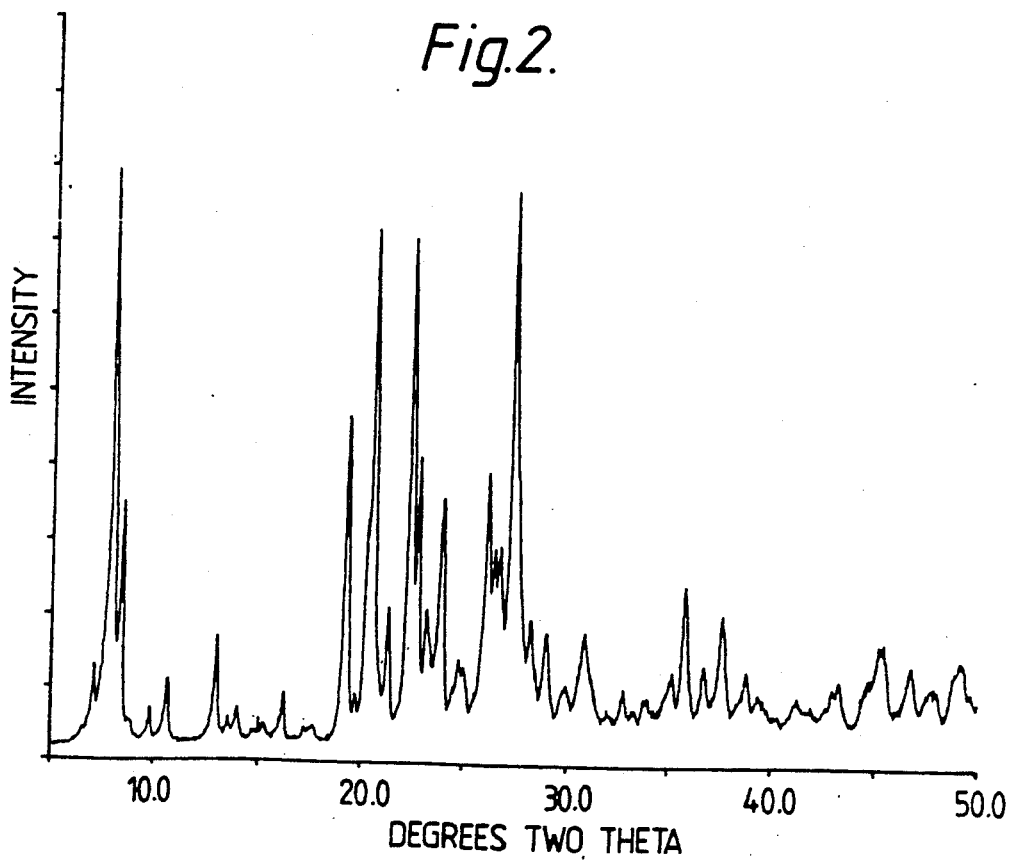

Analysis by powder X-ray diffraction showed the material to be a highly crystalline sample of H-NU-87. The diffraction pattern can be seen in FIG. 2 and Table 5.

EXAMPLE 3

A reaction mixture of a molar composition:

$60\ SiO_2—1.5\ Al_2O_3—10\ Na_2O\ —7.5\ DecBr_2—3000\ H_2O$ was prepared from:
- 36.1 g "CAB-O-SIL" (BDH Ltd)
- 6.982 g "SOAL" 235 (Kaiser Chemicals: molar composition 1.59 $Na_2O$ —1.0 $Al_2O_3$—14.7 $H_2O$)
- 6.09 g Sodium Hydroxide (Analar)
- 31.4 g $DecBr_2$
- 535.2 g Water (deionised)

where $DecBr_2$ is Decamethonium Bromide:

$[(CH_3)_3N(CH_2)_{10}N(CH_3)_3]Br_2$

The mixture was prepared by the following procedure:

The required amount of water was weighed out. About one third was used to prepare a solution (solution A) containing the sodium hydroxide and "SOAL" 235. Solution B was prepared containing the Decamethonium Bromide in about one third of the total water. The remaining water was then used to prepare a dispersion of the silica, "CAB-O-SIL."

Solutions A and B were mixed then added, with stirring, to the dispersion of the "CAB-O-SIL" in water. The resulting mixture was then reacted in a 1 liter stainless steel autoclave at 180° C. The mixture was stirred at 300 rpm using a pitched paddle type impeller.

After 258 hours at temperature the preparation was terminated, crash cooled, and discharged. The solid was separated by filtration, washed with deionised water and dried at 110° C.

Analysis for Na, Si and Al by AAS revealed the following molar composition:

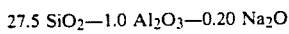
27.5 SiO$_2$—1.0 Al$_2$O$_3$—0.20 Na$_2$O

Figure 3:
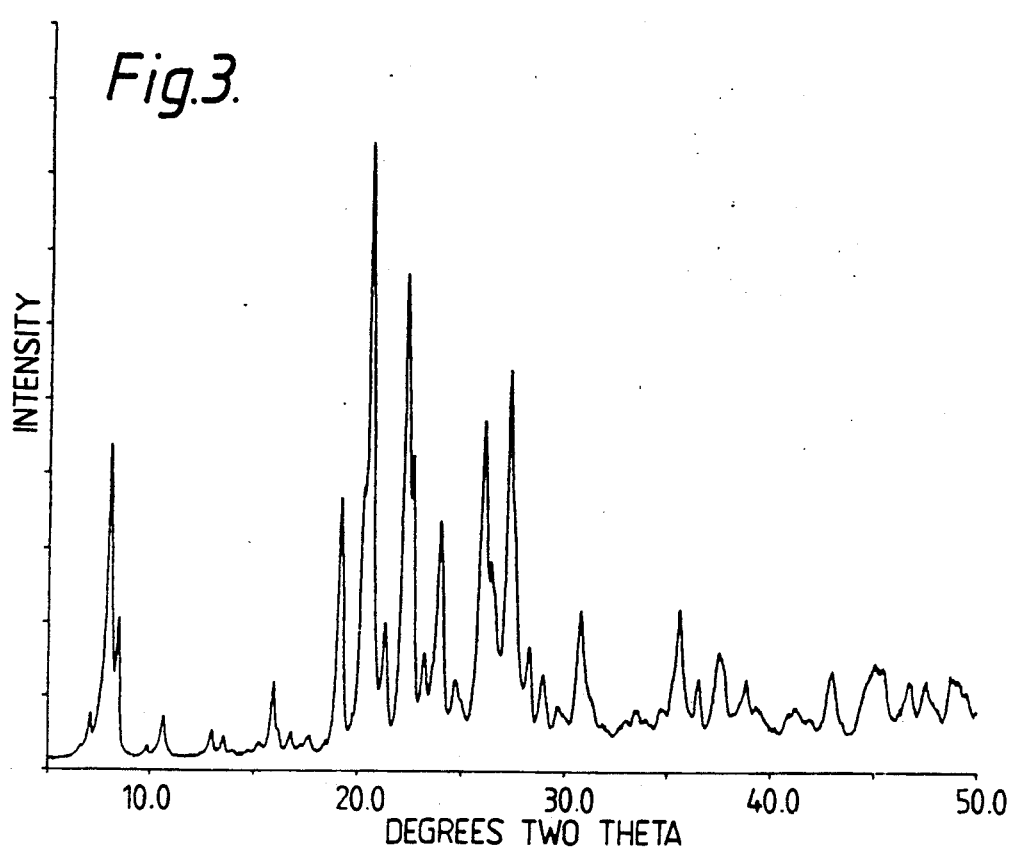

Analysis by X-ray powder diffraction gave the pattern shown in Table 6 and FIG. 3. The product was identified as a highly crystalline sample of NU-87 containing approximately 5% of an analcime impurity.

EXAMPLE 4

Figure 4:
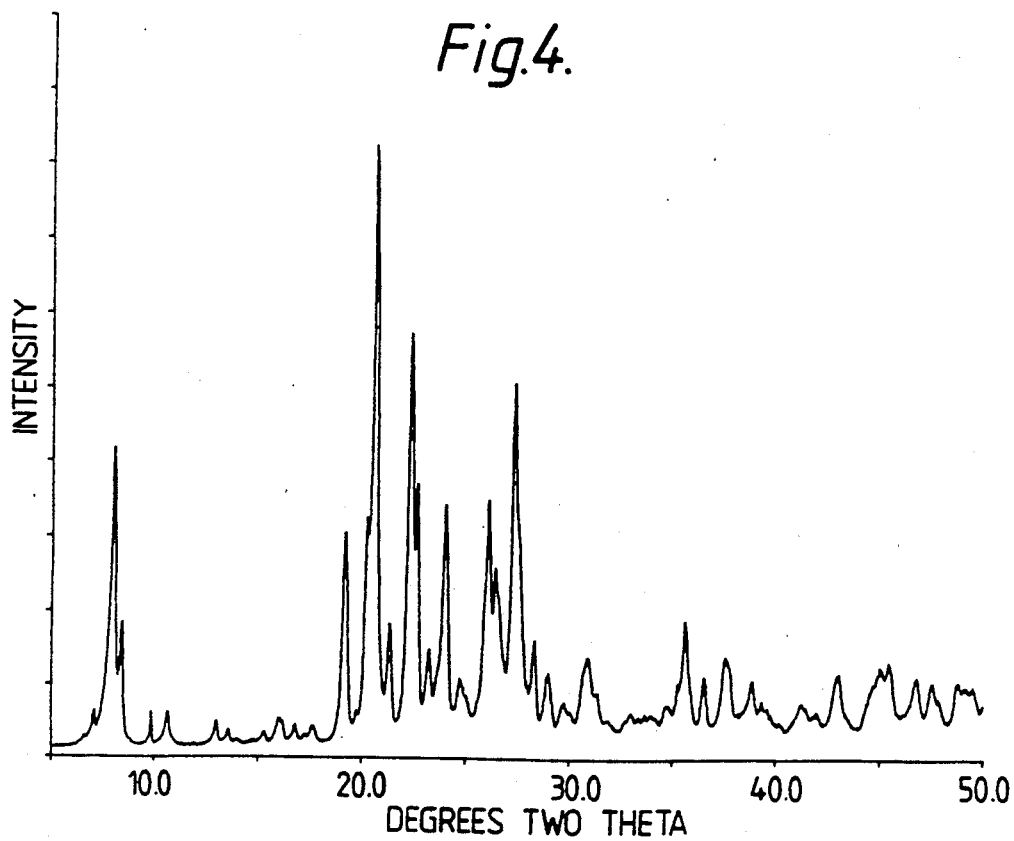

A portion of the product from Example 3 was treated with a molar solution of hydrochloric acid using 50 ml of acid per gram of material. The treatment was carried out at 90° C. for 18 hours after which the solid was removed by filtration, washed with deionised water and dried at 110° C. After two such treatments the product was examined by powder X-ray diffraction and found to be a highly crystalline sample of NU-87 containing no detectable amounts of analcime. The X-ray diffraction pattern can be seen in Table 7 and FIG. 4.

Analysis for Na, Si and Al by AAS revealed the following molar composition:

41.8 SiO$_2$—1.0 Al$_2$O$_3$—0.04 Na$_2$O

EXAMPLE 5

Figure 5:
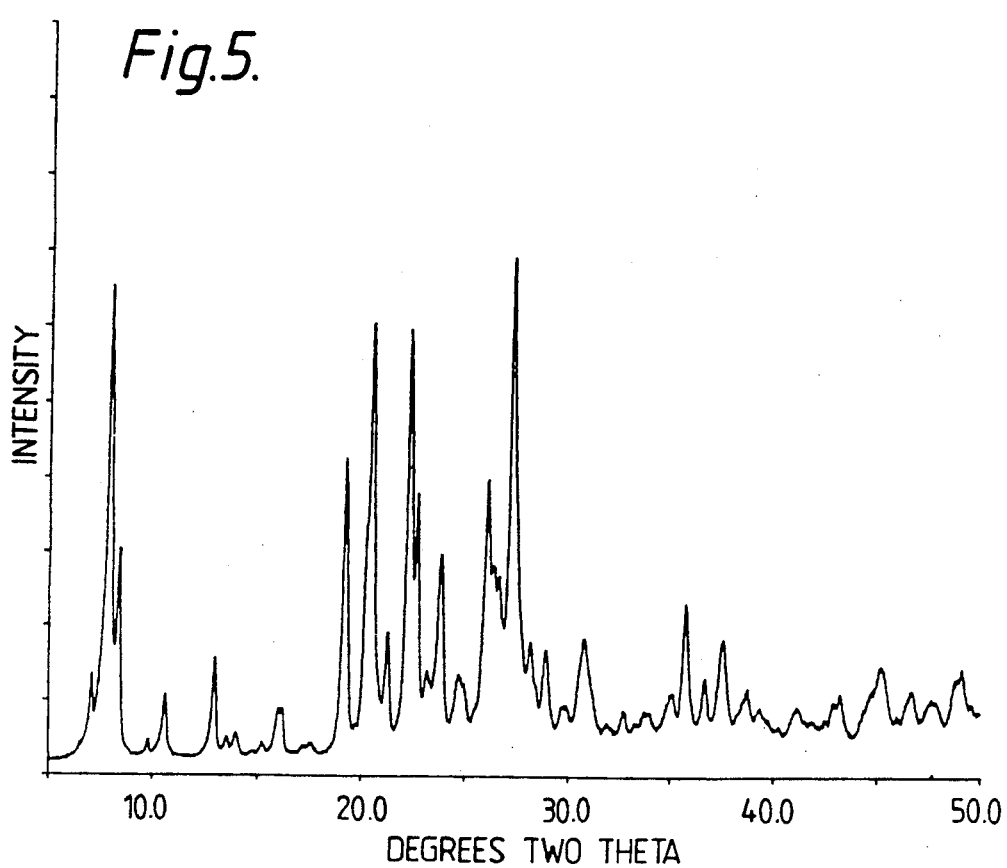

The product from Example 3 was calcined in air for 24 hours at 450° C. followed by 16 hours at 550° C. The resulting material was then ion exchanged, for 4 hours at 60° C. with a 1 molar solution of ammonium chloride using 10 ml of solution per gram of solid calcined product. After ion exchange the material was filtered, washed and dried. This process was repeated. The material was then calcined at 550° C. for 16 hours to generate an H-NU-87 containing approximately 5% of an analcime impurity, as determined by powder X-ray diffraction. The actual X-ray data are given in Table 8 and FIG. 5.

Analysis for Na, Si and Al by AAS revealed the following molar composition:

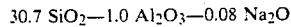
30.7 SiO$_2$—1.0 Al$_2$O$_3$—0.08 Na$_2$O

EXAMPLE 6

Figure 6:
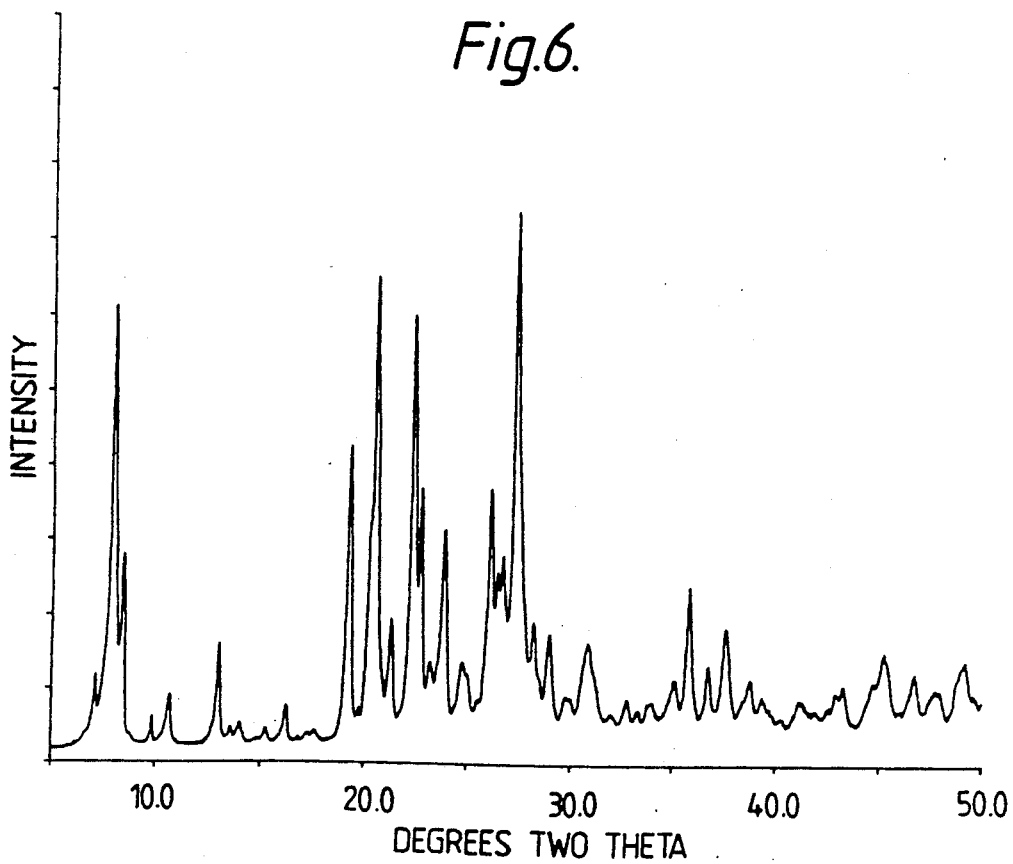

A portion of the product from Example 4 was calcined and ion-exchanged by the same technique as in Example 5. After calcination the material was examined by powder X-ray diffraction and found to be highly crystalline sample of H-NU-87 containing no detectable impurities. The actual pattern can be seen in Table 9 and FIG. 6.

Analysis for Na, Si and Al by AAS showed the material to have the following molar composition:

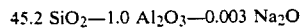
45.2 SiO$_2$—1.0 Al$_2$O$_3$—0.003 Na$_2$O

EXAMPLE 7

Sorption measurements were carried out on a portion of the product from Example 6. The technique was described above and the results can be seen in Table 3.

EXAMPLE 8

A reaction mixture of molar composition:

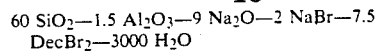
60 SiO$_2$—1.5 Al$_2$O$_3$—9 Na$_2$O—2 NaBr—7.5 DecBr$_2$—3000 H$_2$O was prepared from:
120.2 g "SYTON" X30 (Monsanto: 30% Silica sol)
6.118 g "SOAL" 235 (Kaiser Chemicals: molar composition 1.40 Na$_2$O—Al$_2$O$_3$—12.2 H$_2$O)
5.52 g Sodium Hydroxide (Analar)
31.4 g DecBr$_2$
2.06 g Sodium Bromide
451.9 g Water (deionised)

The molar composition given above does not include sodium present in the "SYTON". The reaction mixture was prepared in a manner similar to Example 1 except that the sodium bromide was added to the sodium hydroxide, "SOAL" 235 and water to form solution A.

The mixture was reacted in a 1 liter stainless steel autoclave at 180° C., with stirring at 300 rpm using a pitched-paddle type agitator.

After 451 hours at reaction temperature the preparation was terminated and crash cooled. The product was discharged, filtered, washed with deionised water and then dried at 110° C.

Figure 7:
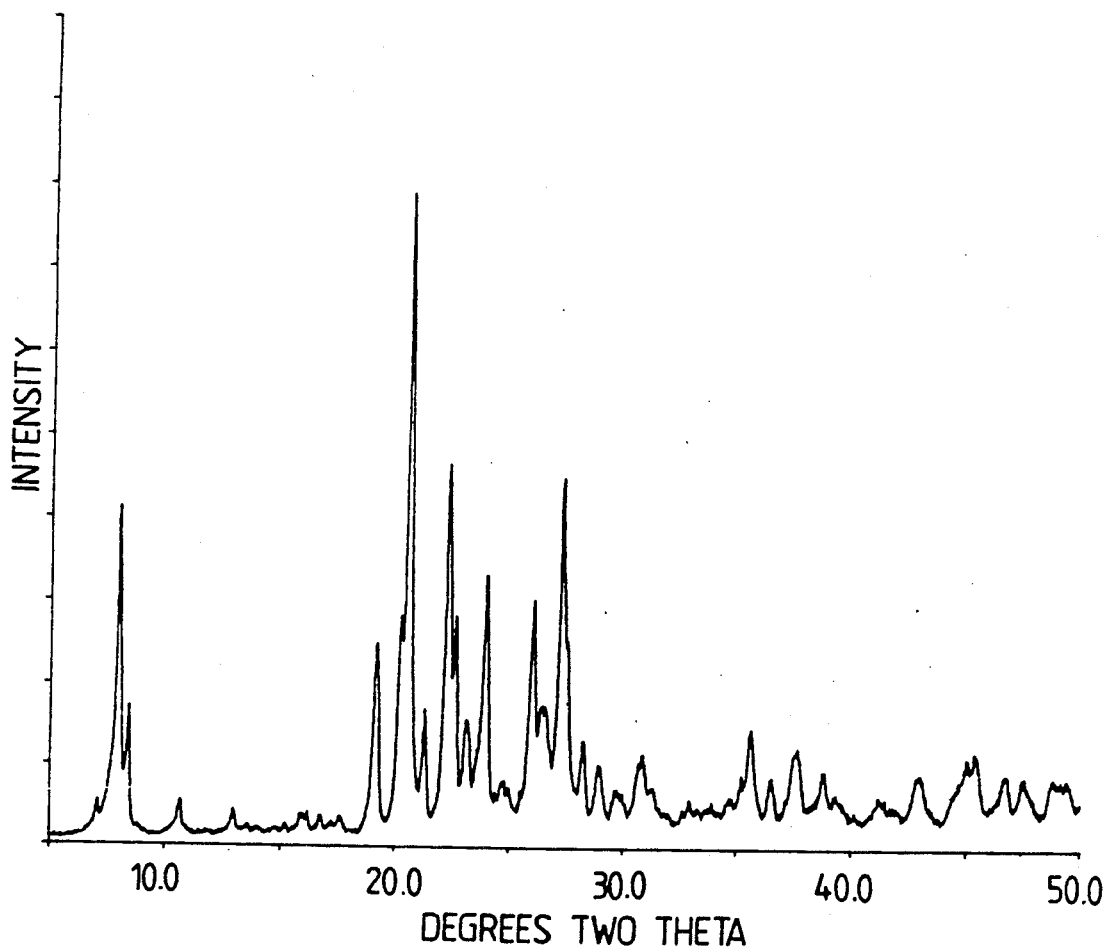

Analysis by powder X-ray diffraction revealed the product to be a substantially pure highly crystalline sample of zeolite NU-87 containing no detectable crystalline impurities. The diffraction pattern is given in FIG. 7 and the interplanar spacings and intensities in Table 10.

Analysis by AAS for Na, Si and Al showed the product to have the following molar composition:

35.5 SiO$_2$—Al$_2$O$_3$—0.07 Na$_2$O

EXAMPLE 9

A reaction mixture of molar composition:

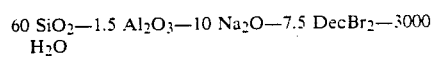
60 SiO$_2$—1.5 Al$_2$O$_3$—10 Na$_2$O—7.5 DecBr$_2$—3000 H$_2$O was prepared from:
120.2 g "SYTON" X30 (Monsanto: 30% Silica sol)
6.118 g "SOAL" 235 (Kaiser Chemicals: molar composition-1.40 Na$_2$O—Al$_2$O$_3$—12.2 H$_2$O)
6.32 g Sodium Hydroxide (Analar)
31.4 g DecBr$_2$
451.7 g Water (deionised)

The molar composition given above does not include sodium present in the "SYTON".

The mixture was prepared as follows:
A—solution containing the sodium hydroxide and "SOAL" 235 in 200 g of water
B—solution containing the DecBr$_2$ in 200 g of water
C—51.7 g of water Solution A was added to the "SYTON" X30, with stirring, over a 30 second period. Mixing was continued for 5 minutes then solution B was added, with stirring, over a 30 second period. Finally, the remaining water, C, was added over a 30 second period. The resulting gel was mixed for a further 5 minutes before being transferred to a 1 liter stainless steel autoclave.

The mixture was reacted at 180° C., with stirring at 300 rpm using a pitched-paddle type impeller. Samples were withdrawn at intervals so that progress of the reaction could be monitored. After a total of 359 hours, at reaction temperature, the preparation was crash cooled to ambient temperature and the product discharged, filtered, washed with deionised water and dried at 110° C.

Analysis by X-ray powder diffraction showed the material to be approximately 80% NU-87 with other crystalline impurities.

Examination of the samples withdrawn from the reaction mixture during progress of the reaction by the pH method described in a paper by J L Casci and B M Lowe in Zeolites, 1983, vol 3, page 186 revealed that the main crystallisation event had occurred, by which we mean a major proportion of the reaction mixture i.e. at least 50.5% crystallised, between a reaction time of 308 and 332 hours.

EXAMPLE 10

Example 9 was repeated except that 1.44 g of NU-87 seed was stirred into the gel before it was transferred to the stainless steel autoclave.

The mixture was reacted at 180° C., with stirring at 300 rpm using a pitched-paddle type impeller. Samples were withdrawn, at intervals, so that progress of the reaction could be monitored.

After a total of 282 hours at reaction temperature the preparation was crash cooled to ambient temperature and the product discharged, filtered, washed with deionised water and dried at 110° C.

Analysis for Na, Al and Si by AAS revealed the following molar composition:

$$35.4\ SiO_2 - 1.0\ Al_2O_3 - 0.09\ Na_2O$$

Analysis by X-ray powder diffraction showed the material to be a highly crystalline sample of NU-87 containing approximately 5% of a mordenite impurity.

Examination of the samples withdrawn from the reaction mixture during progress of the reaction by the pH method referred to in Example 9 revealed that the main crystallisation event had occurred between a reaction time of 140 and 168 hours.

A comparison of Examples 9 and 10 demonstrate that the use of a seed crystal:

(a) reduces the total reaction time required to prepare zeolite NU-87 and (b) increases the purity of NU-87 resulting from a particular reaction mixture.

EXAMPLE 11

The product from Example 10 was calcined in air for 24 hours at 450° C. followed by 16 hours at 550° C. The resulting material was then ion exchanged for 4 hours at 60° C. with a 1 molar solution of ammonium chloride using 10 ml of solution per gram of solid calcined product. After ion exchange the material was filtered, washed and dried. After two such treatments the resulting NH$_4$-NU-87 material was calcined at 550° C. for 16 hours to generate an H-NU-87.

Analysis for Na, Al, and Si by AAS revealed the following molar composition:

$$39.0\ SiO_2 - 1.0\ Al_2O_3 - \text{less than } 0.002\ Na_2O$$

EXAMPLE 12

A reaction mixture of molar composition:

$$60\ SiO_2 - 1.5\ Al_2O_3 - 9\ Na_2O - 7.5\ DecBr_2 - 2\ NaBr - 3000\ H_2O$$

was prepared from:
  300.4 g "SYTON" X30 (Monsanto: 30% silica sol)
  15.29 g "SOAL" 235 (Kaiser Chemicals: molar composition 1.40 Na$_2$O—Al$_2$O$_3$—12.2 H$_2$O)
  13.79 g Sodium Hydroxide (Analar)
  78.4 g Decamethonium Bromide (Fluka)
  5.15 g Sodium Bromide
  1129.6 g Water (deionised)

The molar composition given above does not include sodium present in the "SYTON".

The mixture was prepared as follows:
  A—solution containing the sodium hydroxide and "SOAL" 235 in 500 g of water
  B—solution containing the DecBr$_2$ in 500 g of water
  C—129.6 g of water.

The reaction mixture was prepared in a manner similar to Example 1. The mixture was reacted in a 2 liter stainless steel autoclave at 180° C., with stirring at 300 rpm using two agitators. The lower part of the mixture was stirred using a pitched-paddle type agitator whereas the upper part of the mixture was stirred using a 6-blade turbine type agitator.

After 408 hours at reaction temperature the preparation was terminated by crash cooling. The product was discharged, filtered, washed with deionised water and then dried at 110° C.

Analysis by powder X-ray diffraction showed the material to be a highly crystalline sample of zeolite NU-87 containing no detactable crystalline impurities.

EXAMPLE 13

A portion of the material from Example 12 was calcined in air at 450° C. for 24 hours followed by 16 hours at 550° C. The material was then ion-exchanged for 4 hours with a 1 molar solution of ammonium chloride, at 60° C., using 10 ml of solution per gram of solid calcined product. The material was then filtered, washed with deionised water and dried at 110° C. After two such exchanges the resulting NH$_4$-NU-87 was calcined at 550° C. for 16 hours to generate the hydrogen form, that is, H-NU-87. Analysis by AAS for Si, Al and Na gave the following molar composition:

$$37.9\ SiO_2 - 1.0\ Al_2O_3 - \text{less than } 0.002\ Na_2O$$

EXAMPLE 14

A reaction mixture of molar composition:

$$60\ SiO_2 - 1.5\ Al_2O_3 - 9\ Na_2O - 7.5\ DecBr_2 - 2\ NaBr - 3000\ H_2O$$

was prepared from:
  2.403 kg "SYTON" X30 (Monsanto: 30% silica sol)
  0.1224 kg "SOAL" 235 (Kaiser Chemicals; molar composition 1.40 Na$_2$O—Al$_2$O$_3$—12.2 H$_2$O)
  0.1103 kg Sodium Hydroxide (Analar)
  0.6275 kg Decamethonium Bromide
  0.0412 kg Sodium Bromide
  0.0288 kg NU-87 seed crystals, the product from Example 12
  9.0363 kg Water The molar composition given above does not include the seed crystals or sodium present in the "SYTON".

The mixture was prepared as follows:
  A—solution containing the sodium hydroxide, sodium bromide and "SOAL" 235 in about one third of the total water B—solution containing the DecBr$_2$ in about one third of the total water
C—remaining water The seed crystals were ground to a fine powder and then stirred into the "SYTON" X30. The mixture was transferred to a 19 liter stainless steel autoclave. The mixture was stirred at ambient temperature and a small amount of solution C added. To this mixture solution A was added followed by a small amount of solution C. Solution B was then added followed by the remainder of solution C. The autoclave was sealed and the mixture reacted at 180° C. with stirring and agitation.

After a total of 257 hours at reaction temperature the preparation was terminated, crash cooled and discharged. The product was separated by filtration, washed with water and dried at 110° C. This was labelled product A. It was noted that a small amount of a granular material (product B) remained in the discharge vessel.

Analysis of product A by powder X-ray diffraction revealed the product to be a highly crystalline sample of zeolite NU-87 containing approximately 5% of a crystalline impurity.

EXAMPLE 15

A portion of product A from Example 14 was calcined, in air, at 450° C. for 24 hours followed by 16 hours at 550° C. The resulting material was then contacted for 4 hours at 60° C. with a 1 molar solution of ammonium chloride using 10 ml of solution per gram of solid calcined product. After ion exchange the material was filtered, washed with deionised water and then dried at 110° C. After two such treatments the resulting NH$_4$-NU-87 was calcined at 550° C. for 16 hours to generate H-NU-87.

Analysis for Na, Al and Si by AAS gave the following molar composition:

37 SiO$_2$—Al$_2$O$_3$—0.004 Na$_2$O

EXAMPLE 16

The procedure of Example 15 was repeated using a fresh portion of product A from Example 14.

Analysis, by AAS, for Na, Si and Al gave the following molar composition:

37.0 SiO$_2$—Al$_2$O$_3$—0.002 Na$_2$O

TABLE 4

| X-RAY DATA FOR THE PRODUCT OF EXAMPLE 1 | |
|---|---|
| d (Angstroms) | Relative Intensity (I/Io) |
| 12.53 | 7 |
| 11.11 | 53 |
| 10.56 | 23 |
| 9.01 | 3 |
| 8.34 | 7 |
| 6.83 | 5 |
| 6.54 | 4 |
| 5.56 | 4 |
| 5.47 | 5 |
| 5.30 | 4 |
| 5.15 | 3 |
| 5.02 | 3 |
| 4.62 | 42 |
| 4.52 | 7 |
| 4.40 | 38 |
| 4.32 | 100 |
| 4.17 | 22 |
| 3.99 | 78 |
| 3.93 | 43 |
| 3.85 | 21 |
| 3.84 | 20 |
| 3.71 | 40 |
| 3.60 | 10 |
| 3.44 | 36 |
| 3.42 | 40 |
| 3.38 | 25 |
| 3.35 | 22 |
| 3.27 | 58 |
| 3.24 | 34 |
| 3.16 | 15 |
| 3.08 | 11 |
| 3.01 | 6 |
| 2.90 | 13 |
| 2.86 | 7 |
| 2.74 | 3 |
| 2.72 | 4 |
| 2.69 | 3 |
| 2.64 | 3 |
| 2.59 | 4 |
| 2.55 | 8 |
| 2.52 | 21 |
| 2.46 | 9 |
| 2.45 | 8 |
| 2.40 | 13 |
| 2.39 | 12 |
| 2.32 | 9 |
| 2.29 | 5 |
| 2.19 | 4 |
| 2.11 | 8 |
| 2.10 | 8 |
| 2.04 | 5 |
| 2.01 | 12 |
| 1.99 | 12 |

TABLE 5

| X-RAY DATA FOR THE PRODUCT OF EXAMPLE 2 | |
|---|---|
| d (Angstroms) | Relative Intensity (I/Io) |
| 12.40 | 14 |
| 11.06 | 100 |
| 10.47 | 41 |
| 9.94 | 4 |
| 9.00 | 7 |
| 8.30 | 12 |
| 6.79 | 19 |
| 6.51 | 4 |
| 6.31 | 6 |
| 5.44 | 8 |
| 4.59 | 56 |
| 4.49 | 8 |
| 4.38 | 36 |
| 4.31 | 89 |
| 4.16 | 23 |
| 3.97 | 87 |
| 3.90 | 48 |
| 3.84 | 23 |
| 3.73 | 37 |
| 3.71 | 42 |
| 3.60 | 13 |
| 3.55 | 11 |
| 3.41 | 46 |
| 3.37 | 33 |
| 3.33 | 32 |
| 3.26 | 93 |
| 3.23 | 43 |
| 3.16 | 20 |
| 3.08 | 18 |
| 3.00 | 7 |
| 2.98 | 8 |
| 2.89 | 17 |
| 2.79 | 3 |
| 2.73 | 7 |
| 2.68 | 3 |
| 2.65 | 5 |
| 2.64 | 5 |
| 2.55 | 10 |
| 2.51 | 24 |

TABLE 5-continued
X-RAY DATA FOR THE PRODUCT OF EXAMPLE 2

| d (Angstroms) | Relative Intensity (I/Io) |
|---|---|
| 2.45 | 11 |
| 2.39 | 19 |
| 2.38 | 16 |
| 2.32 | 10 |
| 2.29 | 5 |
| 2.20 | 4 |
| 2.11 | 5 |
| 2.09 | 7 |
| 2.03 | 7 |
| 2.01 | 13 |
| 2.00 | 13 |

TABLE 6
X-RAY DATA FOR THE PRODUCT OF EXAMPLE 3

| d (Angstroms) | Relative Intensity (I/Io) |
|---|---|
| 12.62 | 8 |
| 11.14 | 51 |
| 10.59 | 23 |
| 8.35 | 7 |
| 6.84 | 4 |
| 6.54 | 3 |
| 5.57 | 13 |
| 5.48 | 5 |
| 5.29 | 4 |
| 5.03 | 4 |
| 4.63 | 42 |
| 4.40 | 39 |
| 4.32 | 100 |
| 4.17 | 22 |
| 3.99 | 78 |
| 3.93 | 47 |
| 3.84 | 17 |
| 3.71 | 37 |
| 3.60 | 13 |
| 3.45 | 31 |
| 3.42 | 55 |
| 3.38 | 32 |
| 3.35 | 26 |
| 3.27 | 63 |
| 3.24 | 36 |
| 3.15 | 18 |
| 3.09 | 14 |
| 3.01 | 9 |
| 2.91 | 24 |
| 2.86 | 9 |
| 2.81 | 6 |
| 2.72 | 7 |
| 2.68 | 8 |
| 2.59 | 8 |
| 2.52 | 24 |
| 2.46 | 13 |
| 2.40 | 17 |
| 2.38 | 14 |
| 2.32 | 13 |
| 2.29 | 13 |
| 2.28 | 6 |
| 2.21 | 7 |
| 2.19 | 9 |
| 2.16 | 7 |
| 2.10 | 15 |
| 2.04 | 11 |
| 2.01 | 16 |

TABLE 7
X-RAY DATA FOR THE PRODUCT OF EXAMPLE 4

| d (Angstroms) | Relative Intensity (I/Io) |
|---|---|
| 12.52 | 6 |
| 11.06 | 49 |
| 10.50 | 21 |
| 8.97 | 5 |
| 8.31 | 6 |
| 6.81 | 4 |
| 6.51 | 3 |
| 5.54 | 5 |

TABLE 7-continued
X-RAY DATA FOR THE PRODUCT OF EXAMPLE 4

| d (Angstroms) | Relative Intensity (I/Io) |
|---|---|
| 5.46 | 4 |
| 5.29 | 4 |
| 5.01 | 3 |
| 4.62 | 35 |
| 4.50 | 6 |
| 4.39 | 37 |
| 4.31 | 100 |
| 4.16 | 21 |
| 3.98 | 69 |
| 3.92 | 43 |
| 3.83 | 17 |
| 3.70 | 40 |
| 3.61 | 11 |
| 3.44 | 22 |
| 3.4 | 41 |
| 3.37 | 30 |
| 3.35 | 24 |
| 3.27 | 60 |
| 3.23 | 33 |
| 3.15 | 18 |
| 3.09 | 12 |
| 3.08 | 13 |
| 3.01 | 8 |
| 2.97 | 6 |
| 2.92 | 12 |
| 2.89 | 15 |
| 2.85 | 9 |
| 2.81 | 5 |
| 2.71 | 6 |
| 2.68 | 5 |
| 2.66 | 5 |
| 2.63 | 5 |
| 2.59 | 7 |
| 2.54 | 11 |
| 2.52 | 21 |
| 2.46 | 12 |
| 2.40 | 15 |
| 2.38 | 13 |
| 2.32 | 11 |
| 2.29 | 8 |
| 2.24 | 4 |
| 2.19 | 7 |
| 2.15 | 6 |
| 2.10 | 13 |
| 2.03 | 10 |
| 2.01 | 13 |

TABLE 8
X-RAY DATA FOR THE PRODUCT OF EXAMPLE 5

| d (Angstroms) | Relative Intensity (I/Io) |
|---|---|
| 12.41 | 17 |
| 11.10 | 96 |
| 10.48 | 42 |
| 8.99 | 4 |
| 8.31 | 13 |
| 6.79 | 21 |
| 6.51 | 4 |
| 6.33 | 5 |
| 5.53 | 10 |
| 5.45 | 10 |
| 4.60 | 61 |
| 4.50 | 7 |
| 4.38 | 43 |
| 4.32 | 88 |
| 4.16 | 26 |
| 3.98 | 87 |
| 3.91 | 52 |
| 3.83 | 17 |
| 3.72 | 42 |
| 3.60 | 17 |
| 3.56 | 14 |
| 3.41 | 57 |
| 3.37 | 40 |
| 3.34 | 38 |
| 3.26 | 100 |
| 3.16 | 24 |
| 3.08 | 22 |

TABLE 8-continued
X-RAY DATA FOR THE PRODUCT OF EXAMPLE 5

| d (Angstroms) | Relative Intensity (I/Io) |
|---|---|
| 3.07 | 20 |
| 3.00 | 11 |
| 2.98 | 11 |
| 2.92 | 17 |
| 2.90 | 25 |
| 2.80 | 7 |
| 2.73 | 10 |
| 2.65 | 9 |
| 2.63 | 10 |
| 2.55 | 14 |
| 2.51 | 31 |
| 2.45 | 17 |
| 2.39 | 24 |
| 2.32 | 14 |
| 2.29 | 11 |
| 2.24 | 7 |
| 2.20 | 10 |
| 2.15 | 8 |
| 2.11 | 11 |
| 2.09 | 13 |
| 2.03 | 13 |
| 2.00 | 18 |

TABLE 9
X-RAY DATA FOR THE PRODUCT OF EXAMPLE 6

| d (Angstroms) | Relative Intensity (I/Io) |
|---|---|
| 12.44 | 14 |
| 11.12 | 84 |
| 10.52 | 37 |
| 9.01 | 6 |
| 8.33 | 10 |
| 6.81 | 19 |
| 6.53 | 4 |
| 6.32 | 4 |
| 5.81 | 3 |
| 5.45 | 8 |
| 4.60 | 56 |
| 4.39 | 39 |
| 4.32 | 89 |
| 4.17 | 25 |
| 3.98 | 82 |
| 3.91 | 49 |
| 3.84 | 16 |
| 3.73 | 41 |
| 3.60 | 16 |
| 3.56 | 14 |
| 3.41 | 49 |
| 3.37 | 33 |
| 3.34 | 36 |
| 3.26 | 100 |
| 3.16 | 24 |
| 3.08 | 22 |
| 3.01 | 10 |
| 2.98 | 9 |
| 2.90 | 20 |
| 2.86 | 12 |
| 2.80 | 7 |
| 2.73 | 9 |
| 2.69 | 7 |
| 2.65 | 8 |
| 2.63 | 9 |
| 2.55 | 13 |
| 2.51 | 30 |
| 2.45 | 16 |
| 2.39 | 23 |
| 2.32 | 13 |
| 2.29 | 10 |
| 2.24 | 6 |
| 2.20 | 9 |
| 2.16 | 7 |
| 2.13 | 8 |
| 2.11 | 11 |
| 2.09 | 12 |
| 2.03 | 12 |
| 2.01 | 18 |

TABLE 9-continued
X-RAY DATA FOR THE PRODUCT OF EXAMPLE 6

| d (Angstroms) | Relative Intensity (I/Io) |
|---|---|
| 2.00 | 16 |

TABLE 10
X-RAY DATA FOR THE PRODUCT OF EXAMPLE 8

| d (Angstroms) | Relative Intensity (I/Io) |
|---|---|
| 12.46 | 6 |
| 11.05 | 53 |
| 10.50 | 20 |
| 8.29 | 6 |
| 6.82 | 4 |
| 5.58 | 3 |
| 5.47 | 4 |
| 5.28 | 3 |
| 5.02 | 3 |
| 4.62 | 31 |
| 4.39 | 35 |
| 4.31 | 100 |
| 4.16 | 20 |
| 3.98 | 60 |
| 3.92 | 35 |
| 3.85 | 20 |
| 3.82 | 16 |
| 3.71 | 43 |
| 3.59 | 9 |
| 3.49 | 7 |
| 3.42 | 38 |
| 3.38 | 21 |
| 3.34 | 20 |
| 3.26 | 57 |
| 3.23 | 30 |
| 3.16 | 16 |
| 3.15 | 14 |
| 3.09 | 12 |
| 3.07 | 11 |
| 3.01 | 7 |
| 2.98 | 7 |
| 2.91 | 12 |
| 2.90 | 14 |
| 2.86 | 8 |
| 2.71 | 6 |
| 2.68 | 5 |
| 2.64 | 5 |
| 2.59 | 6 |
| 2.54 | 10 |
| 2.52 | 16 |
| 2.46 | 10 |
| 2.40 | 14 |
| 2.38 | 14 |
| 2.32 | 11 |
| 2.29 | 7 |
| 2.24 | 4 |
| 2.19 | 7 |
| 2.16 | 5 |
| 2.10 | 10 |
| 2.07 | 4 |
| 2.04 | 7 |
| 2.01 | 12 |
| 2.00 | 14 |
| 1.99 | 11 |

In the catalysts according to the invention $XO_2$ is preferably silica and $Y_2O_3$ is preferably alumina. Such catalysts may be used in a wide variety of catalytic processes and using a wide variety of feedstocks.

Catalytically useful forms of zeolite NU-87 include the hydrogen and ammonium forms, prepared by the methods hereinbefore described.

Catalysts according to the invention comprising NU-87 may also comprise one or more elements, especially metals or cations thereof, or compounds of said elements, especially metal oxides. Such catalysts may be prepared by ion-exchange or impregnation of zeolite NU-87 with the said element, cation or compound, or a suitable precursor of said cation or compound. Such ion-exchange or impregnation may be carried out on the as-prepared zeolite NU-87, the calcined form, the hydrogen form and/or the ammonium form and/or any other exchanged form.

In cases where a metal-containing form of zeolite NU-87 is prepared by ion-exchange it may be desirable to effect complete exchange of the metal, by which is meant that substantially all of the exchangeable sites are occupied by the metal. In most cases, however, it is preferable to effect only partial exchange of the metal, the remaining sites being occupied by another cation especially hydrogen or ammonium cations. In some cases it may be desirable to introduce two or more metal cations by ion exchange.

In cases where zeolite NU-87 is impregnated with a metal compound to form a catalyst, the metal compound may be added in any suitable quantity, but 20% by weight is generally sufficient for most applications; for some applications up to 10% by weight is sufficient, and quantities of up to 5% are often appropriate. Impregnation may be carried out by any suitable method known in the art of catalyst preparation.

Metal-exchanged forms or forms in which a metal compound has been impregnated may be used as such or they may be treated to produce an active derivative. Treatments include reduction, for example in an atmosphere comprising hydrogen, to produce a metal or other reduced forms. Such treatments may be carried out at a suitable stage in the catalyst preparation or may conveniently be carried out in the catalytic reactor.

Catalytic compositions comprising zeolite NU-87 can, if desired, be associated with an inorganic matrix which may be either inert or catalytically active. The matrix may be present solely as a binding agent to hold the zeolite particles together, possibly in a particular shape or form, for example as a pellet or extrudate, or it may function as an inert diluent, for example to control the activity per unit weight of catalyst. When the inorganic matrix or diluent is itself catalytically active it can thereby form an effective part of the zeolite/matrix catalyst composition. Suitable inorganic matrices and diluents include conventional catalyst support materials such as silica, the various forms of alumina, clays such as bentonites, montmorillonites, sepiolite, attapulgite, Fullers Earth and synthetic porous materials such as silica-alumina, silica-zirconia, silica-thoria, silica-beryllia or silica-titania. Combinations of matrices are contemplated within the present invention, especially combinations of inert and catalytically-active matrices.

When zeolite NU-87 is associated with an inorganic matrix material or a plurality thereof, the proportion of matrix material or materials in the total composition usually amounts to up to about 90% by weight, preferably up to 50% by weight, more preferably up to 30% by weight.

For some applications another zeolite or molecular sieve may be used in conjunction with zeolite NU-87 to form a catalyst. Such a combination may be used as such or associated with one or more matrix materials hereinbefore described. A particular example of the use of such an overall composition is as a fluid catalytic cracking catalyst additive, in which case zeolite NU-87 is preferably used in an amount of 0.5 to 5% by weight of the total catalyst.

For other applications zeolite NU-87 may be combined with another catalyst, such as platinum on alumina.

Any convenient method of mixing zeolite NU-87 with an inorganic matrix and/or another zeolite material, may be employed, especially that suited to the final form in which the catalyst is used, for example extrudates, pellets or granules.

If zeolite NU-87 is used to form a catalyst in conjunction with a metal component (for example, a hydrogenation/dehydrogenation component or other catalytically active metal) in addition to an inorganic matrix, the metal component can be exchanged or impregnated into the zeolite NU-87 itself before addition of the matrix material or into the zeolite-matrix composition. For some applications it may be advantageous to add the metal component to the whole or part of the matrix material before mixing the latter with the zeolite NU-87.

A wide range of hydrocarbon conversion catalysts comprising zeolite NU-87 can be prepared by ion-exchange or impregnation of the zeolite with one or more cations or oxides derived from elements selected from Cu, Ag, Ga, Mg, Ca, Sr, Zn, Cd, B, Al, Sn, Pb, V, P, Sb, Cr, Mo, W, Mn, Re, Fe, Co, Ni and noble metals.

In cases where catalysts comprising zeolite NU-87 contain one or more hydrogenation/dehydrogenation components such as the metals Ni, Co, Pt, Pd, Re and Rh, such components can be introduced by ion-exchange or impregnation of a suitable compound of the metal.

Catalyst compositions comprising zeolite Nu-87 may find application in reactions involving saturated and unsaturated aliphatic hydrocarbons, aromatic hydrocarbons, oxygenated organic compounds and organic compounds containing nitrogen and/or sulphur as well as organic compounds containing other functional groups.

In general, catalyst compositions comprising zeolite NU-87 can be usefully employed in reactions involving isomerisation, transalkylation and disproportionation, alkylation and de-alkylation, dehydration and hydration, oligomerisation and polymerisation, cyclisation, aromatisation, cracking, hydrogenation and dehydrogenation, oxidation, halogenation, synthesis of amines, hydrodesulphurisation and hydrodenitrification, ether formation and synthesis of organic compounds in general.

The above processes may be carried out in either the liquid or vapour phase under conditions which are chosen as suitable for each individual reaction. For example, the reactions carried out in the vapour phase may involve the use of fluid bed, fixed bed or moving bed operations. Process diluents may be used when required. Depending upon the particular process, suitable diluents include inert gases (such as nitrogen or helium), hydrocarbons, carbon dioxide, water or hydrogen. The diluent may be inert or it may exert a chemical effect. It may be an advantage, especially in cases where hydrogen is used, to include a metal component, such as a hydrogenation/dehydrogenation component, for example one or more of the metals, Ni, Co, Pt, Pd, Re or Rh as part of the catalyst composition.

According to a further aspect of the present invention we provide a hydrocarbon conversion process which comprises contacting an alkylbenzene or a mixture of alkylbenzenes under isomerisation conditions in the vapour or liquid phase with a catalyst comprising zeolite NU-87.

Isomerisation reactions for which catalysts comprising zeolite NU-87 are of particular use are those involving alkanes and substituted aromatic molecules, especially xylenes. Such reactions may include those which can be carried out in the presence of hydrogen. Catalyst compositions containing zeolite NU-87 which are of particular use in isomerisation reactions include those in which the NU-87 is in its acid (H) form, cation-exchanged form, or other metal-containing forms or combinations thereof. Especially useful are those forms in which the metal is a hydrogenation/dehydrogenation component such as Ni, Co, Pt, Pd, Re or Rh.

Particular isomerisation reactions in which a catalyst comprising NU-87 may be found useful include xylene isomerisation and hydroisomerisation of xylenes, paraffin, in particular $C_4$ to $C_{10}$ normal hydrocarbons, or olefin isomerisation and catalytic dewaxing.

Xylene isomerisation and hydroisomerisation may be carried out in the liquid or vapour phase. In the liquid phase, suitable isomerisation conditions include a temperature in the range 0°–350° C., a pressure in the range 1–200 atmospheres absolute, preferably 5–70 atmospheres absolute, and when conducted in a flow system, a weight hourly space velocity (WHSV) preferably in the range 1–30 $hr^{-1}$ based on the total catalyst composition. Optionally, a diluent may be present, suitably one or more of those having a critical temperature higher than the isomerisation conditions being used. The diluent, if present, may comprise 1–90% by weight of the feed. Vapour phase xylene isomerisation and hydroisomerisation reactions are most suitably carried out at a temperature in the range 100°–600° C., preferably 200°–500° C., at a pressure in the range 0.5–100 atmosphere absolute, preferably 1–50 atmospheres absolute, and at a WHSV up to 80 based on the total catalyst composition.

When xylene isomerisation is conducted in the presence of hydrogen (in the vapour phase), the preferred hydrogenation/dehydrogenation component is Pt or Ni. The hydrogenation/dehydrogenation component is usually added in an amount of between 0.05 and 2% by weight of the total catalyst. Additional metals and/or metal oxides may be present in the catalyst composition.

In xylene isomerisation, ethylbenzene may be present in the xylene feed in amounts up to 40% by weight. Over catalyst compositions comprising zeolite NU-87 the ethylbenzene will undergo transalkylation with itself, and with xylenes, to form heavier and lighter aromatic compounds. The ethylbenzene will also react to form benzene and light gas, particularly at temperatures above 400° C. With such xylene feeds containing ethylbenzene, when reaction is carried out in the presence of hydrogen over a catalyst composition comprising zeolite NU-87 together with a hydrogenation/dehydrogenation component, some of the ethylbenzene will isomerise to xylenes. It may also be an advantage to carry out xylene isomerisation reactions in the presence of a hydrocarbon compound, especially a paraffin or naphthene with or without the additional presence of hydrogen. The hydrocarbon appears to improve catalyst performance in that reactions which lead to xylenes loss are suppressed and, particularly when reactions are carried out in the absence of hydrogen, catalyst life is extended.

According to yet a further aspect of the present invention we provide a hydrocarbon conversion process which comprises contacting one or more alkylated aromatic compounds under transalkylation conditions in the vapour or liquid phase with a catalyst comprising zeolite NU-87.

Catalysts comprising zeolite NU-87 are of especial value in transalkylation and disproportionation reactions, in particular those reactions involving mono-, di-, tri- and tetra-alkyl substituted aromatic molecules, especially toluene and xylenes.

Catalyst compositions comprising NU-87 which are of particular use in transalkylation and disproportionation reaction include those in which the NU-87 component is in its acid (H) form, its cation-exchanged form, or other metal-containing forms or combinations thereof. Especially useful is the acid form and those forms in which the metal is a hydrogenation/dehydrogenation component such as Ni, Co, Pt, Pd, Re or Rh.

Particular examples of important processes include toluene disproportionation and the reaction of toluene with aromatic compounds containing 9 carbon atoms, for example trimethyl benzenes.

Toluene disproportionation can be conducted in the vapour phase either in the presence or absence of hydrogen, although the presence of hydrogen is preferred as this helps to suppress catalyst deactivation. The most suitable reaction conditions are: temperatures in the range 250°–650° C., preferably 300°–550° C.; pressures in the range 0.3–100 atmospheres absolute, preferably 1–50 atmospheres absolute; weight hourly space velocity up to 50 (based on the total catalyst composition).

When toluene disproportionation is conducted in the presence of hydrogen the catalyst may, optionally, contain a hydrogenation/dehydrogenation component. The preferred hydrogenation/dehydrogenation component is Pt, Pd, or Ni. The hydrogenation/dehydrogenation component is normally added in a concentration of up to 5% by weight of the total catalyst composition. Additional metals and/or metal oxides may be present in the catalyst composition, for example up to 5% by weight of the total catalyst composition.

The present invention further provides a hydrocarbon conversion process which comprises reacting an olefinic or aromatic compound with a suitable alkylating compound under alkylating conditions in the vapour or liquid phase over a catalyst comprising zeolite NU-87.

Among the alkylation reactions for which catalysts comprising zeolite NU-87 are of particular use are the alkylation of benzene or substituted aromatic molecules with methanol or an olefin or ether. Specific examples of such processes include toluene methylation, ethylbenzene synthesis, and the formation of ethyl toluene and cumene. Alkylation catalysts used in processes according to this further aspect of the invention may comprise further materials, especially metal oxides which may improve catalytic performance.

Catalysts comprising zeolite NU-87 may find application in reactions involving the dehydration of alcohols, for example methanol and higher alcohols, to form hydrocarbons, including olefins and gasoline. Other feedstocks for dehydration reactions involving a catalyst comprising NU-87 include ethers, aldehydes and ketones.

By the use of a catalyst comprising NU-87, hydrocarbons can be generated by carrying out oligomerisation, cyclisation and/or aromatisation reactions on unsaturated compounds such as ethene, propene butenes, on saturated compounds such as propane or butane or mixtures of hydrocarbons such as light napthas. For some reactions, particularly aromatisation reactions, the catalyst may usefully comprise a metal or metal oxide, especially platinum, gallium, zinc or their oxides.

Catalysts comprising NU-87 are of use in a variety of cracking reactions, including the cracking of olefins, paraffins or aromatics or mixtures thereof. Of particular value is the use of zeolite NU-87 as a fluid catalytic cracking catalyst additive to improve the product of the cracking reaction. Zeolite NU-87 may also be used as a component of a catalyst in catalytic dewaxing or hydrocracking processes.

Hydrogenation/dehydrogenation processes, for example the dehydrogenation of alkanes to the corresponding olefins, are suitably carried out by contacting the appropriate feedstock under appropriate conditions with a catalyst comprising zeolite NU-87, especially when the latter also comprises a hydrogenation/dehydrogenation component such as Ni, Co, Pt, Pd, Re or Ru.

Zeolite NU-87 is useful as a component in a catalyst for the preparation of amines, for example the production of methylamines from methanol and ammonia.

Zeolite Nu-87 is also a useful catalyst for the formation of ethers, particularly by the reaction of two alcohols or by the reaction of an olefin with an alcohol, especially the reaction of methanol with isobutene or pentenes.

The invention relating to catalysts comprising NU-87 and processes using these catalysts is illustrated by the following Examples.

EXAMPLE 17

Cracking of N-Butane

EXAMPLE 17a

The cracking of n-butane over H-NU-87 was examined using a portion of the material from Example 5. The procedure followed that described by: H Rastelli Jr., BM Lok, J A Duisman, D E Earls and J T Mullhaupt, Canadian Journal of Chemical Engineering, Volume 60, February 1982, pages 44–49. The contents of which are incorporated herein by reference.

A portion of the product from Example 5 was pelleted, broken down and sieved to give a 500–1000 micron size fraction. 0.6293 g of this material, which had been previously dehydrated by heating at 500° C. for 4 hours in a stream of dry nitrogen, were charged to a stainless-steel micro reactor. Before carrying out the reaction the material was heated for 18 hours in stream of dry air.

A feed containing 2.1% v/v n-butane, 15.2% v/v nitrogen and 82.7% v/v helium was passed over the catalyst. The catalyst was maintained at a temperature of 500° C. The cracked products were analysed by gas chromatography. This showed that the zeolite cracked n-butane to $C_1$–$C_3$ hydrocarbons. At a feed flow rate of 50 $cm^3$ per minute an n-butane conversion of 60% was measured which corresponds to a $k_A$ of 72.8 $cm^3/g$ min using the equation given in the above reference.

EXAMPLE 17b

The cracking of n-butane over H-NU-87 was examined using a portion of the material from Example 15. The procedure followed that described in Example 17a.

A portion of the product from Example 15 was pelleted, broken-down and sieved to give a 500–1000 micron size fraction. 0.4006 g of this material was charged to a stainless-steel micro reactor (internal diameter 4.6 mm) and supported on glass wool and glass balls. The material was then dehydrated "in situ" by heating at 500° C. for 18 hours in a stream of dry nitrogen.

A feed containing 2.0 mole % n-butane, 15.2% mole nitrogen and 82.8 mole % helium was passed over the catalyst bed. The catalyst bed was maintained at a temperature of 500° C. and atmospheric pressure. The cracked products were analysed by gas chromatography. At a feed flow rate of 96.8 $cm^3$ per minute an n-butane conversion of 41.7% was measured. This corresponds to a $k_A$ of 144.8 $cm^3/g$ min. The feed flow rate was then reduced to 51.7 $cm^3$ per minute and gave an n-butane conversion of 62.1%. This corresponds to a $k_A$ of 139.0 $cm^3/g$ min.

The zeolite cracked the n-butane giving the following products:

| Feed flow rate ($cm^3$/min) | Weight % | | | | |
| --- | --- | --- | --- | --- | --- |
| | $CH_4$ | $C_2H_6$ | $C_2H_4$ | $C_3H_8$ | $C_3H_6$ |
| 96.8 | 8.9 | 11.0 | 23.0 | 33.5 | 23.6 |
| 51.7 | 9.2 | 11.1 | 22.3 | 39.5 | 17.9 |

The zeolite was then regenerated by heating at 500° C. for 25.5 hours in a stream of dry air. The feed was reintroduced at a feed flow rate of 96.8 $cm^3$ per minute and a n-butane conversion of 43.3% was measured. This corresponds to a $k_A$ of 152.2 $cm^3/g$ min. The feed flow rate was reduced to 50.7 $cm^3$ per minute and a n-butane conversion of 62.9% was measured. This corresponds to a $k_A$ of 139.1 $cm^3/g$ min.

These examples show that zeolite NU-87 is an active catalyst for n-butane cracking.

The following example illustrates the use of zeolite NU-87 in Transalkylation/Disproportionation reactions.

EXAMPLE 18

Disproportionation of Toluene

A portion of the material from Example 5 was pelleted, broken down and sieved to give aggregates of between 425 and 1000 microns. 0.5 g of this material was placed in a 5 mm internal diameter stainless steel reactor and calcined at 500° C. in air for 16 hours at atmospheric pressure. The air was replaced by nitrogen and the reactor and contents were cooled to 350° C. Hydrogen was then passed through the reactor and the pressure raised to 20 bar. The flow rate was set at 2.59 liters per hour as measured at atmospheric pressure. After 1 hour, toluene was introduced into the hydrogen stream at a rate of 2.85 mls of liquid per hour. The mole ratio of hydrogen to toluene was 4 to 1.

The compositions of the product in weight percent at various times are given in Table 11. This shows that zeolite NU-87 is highly active and selective catalyst for the disproportionation of toluene.

The following examples illustrate the use of zeolite NU-87 in isomerisation reactions.

EXAMPLE 19

Hhydroisomerisation of N-Pentane

EXAMPLE 19a

A slurry consisting of 2.31 g of the material from Example 15, 0.85 ml of a chloroplatinic acid solution and 28 ml of deionised water was stirred in a closed vessel at room temperature for 4 hours. (The chloroplatinic acid solution contained the equivalent of 0.368 g of platinum in 25 ml of deionised water). Water was then evaporated from the mixture using a rotary evaporator and the resultant solid calcined in air at 500° C. for 3 hours.

The platinum impregnated zeolite powder thus produced was analysed by Atomic Adsorption Spectroscopy (AAS) and found to contain 0.41 weight percent platinum. The powder was pelleted, broken-down and sieved to give a 500 to 1000 micron size fraction. 1.12 g of this material was transferred to a stainless steel reactor (internal diameter 4.2 mm) and reduced under a stream of hydrogen at 250° C. and a pressure of 450 psig for 24 hours. Liquid n-pentane, which had previously been dried over a molecular sieve, was vaporised and mixed with hydrogen gas to produce a mixture with a molar ratio of $H_2$ to pentane of 1.5:1. This mixture was passed over the catalyst bed at a weight hourly space velocity (WHSV) of 1.1 hour$^{-1}$ based on the n-pentane at a pressure of 450 psig and a temperature of 250° C. The product leaving the reactor bed was analysed by on line chromatography. It was found to contain 72% isopentane and 28% n-pentane. This corresponds to a conversion of 72%. This product composition is equivalent to the limiting thermodynamic equilibrium mixture of n- and iso-pentane at 250° C. Thus, this example demonstrates the high activity of the Pt-NU-87 catalyst in n-pentane hydroisomerisation.

Example 19b

X—solution of 0.150 g of $Pt(NH_3)_4Cl_2$ in 5 ml of deionised water adjusted to pH 10 using concentrated ammonia solution Y—solution of 2M $NH_4NO_3$ adjusted to pH 10 using concentrated ammonia solution Z—dilute ammonia solution of pH 10.

A solution comprising 0.66 ml of X, 5.9 ml of Y and 15 ml of Z was stirred with 2.62 g of material from Example 15 for 48 hours at 90° C. The zeolite was filtered, washed with dilute ammonia solution (pH 10 and then calcined in static air as follows:
(a) temperature increasing from 25° to 100° C. over a period of 2 hours;
(b) 100° C. for 3 hours;
(c) temperature increasing from 100° to 395° C. over a period of 6 hours;
(d) 395° C. for 2 hours;
(e) temperature increasing from 395° to 550° C. over a period of 4 hours; and
(f) 550° C. for 3 hours The resulting catalyst powder was analysed by AAS and found to contain 0.28 weight percent platinum. The powder was pelleted, broken down and sieved to give a 500 to 1000 micron size fraction.

0.98 g of this material was transferred to the reactor described in Example 19a. The material was reduced at a temperature of 251° C. and a pressure of 450 psig for 24 hours. Hydrogen and liquid n-pentane, molar ratio $H_2$ to pentane of 1.2:1 was prepared using the method described in Example 19a. Finally the procedure described in Example 19a was used to test the catalyst. The weight hourly space velocity of the n-pentane over the catalyst bed was 1.0 hour$^{-1}$. The product contained 67% iso-pentane and 33% n-pentane.

This example demonstrates that a platinum containing form of zeolite NU-87, prepared either by impregnation or ion exchange, is highly active for the hydroisomerisation of n-pentane.

EXAMPLE 20

Hydroisomerisation of Xylenes

A portion of the material from Example 5 was pelleted, broken down and sieved to give aggregates of between 425 and 1000 microns. 0.1 g of this material were placed in a 2 mm internal diameter stainless steel tubular reactor and calcined in air for 16 hours at 500° C. The air was purged with nitrogen and the reactor and contents were cooled to 400° C. Hydrogen was introduced into the reactor at a flow rate of 4.9 liters per hour, as measured at atmospheric pressure, and the pressure was increased to 80 psig. After 1 hour the temperature was reduced to 275° C. A mixture of $C_8$ aromatic hydrocarbons was added to the hydrogen stream at a rate of 5 ml of liquid per hour. The mole ratio of hydrogen to hydrocarbon was 5 to 1. The temperature was raised in steps to 400° C., at which temperature reasonable conversions were obtained. The temperature was further increased to 450° C. and then to 480° C.

The feed and product compositions are given in Table 12.

EXAMPLE 21

Low Pressure Isomerisation in the Absence of Hydrogen

A portion of the material from Example 5 was pelleted, broken down and sieved to give aggregates of between 425 and 1000 microns. 0.5 g of the aggregates were placed in a 5 mm internal diameter stainless steel tubular reactor and calcined for 16 hours at 500° C. The air was purged with nitrogen and the reactor and contents were cooled to 350° C. and a mixture of $C_8$ aromatics were passed over the catalyst at a rate of 21 ml of liquid per hour. Table 13 gives the feed and product compositions after 10 hours on line.

These examples show that zeolite NU-87 can be used to catalyse the isomerisation of xylenes with very little xylenes loss. In addition, the loss of ethylbenzene, desirable for efficient xylene isomerisation plant operation, was quite high.

The following examples illustrate the use of catalyst compositions containing zeolite NU-87 in alkylation reactions.

EXAMPLE 22

Methylation of Toluene in the Presence of Hydrogen

The catalyst material which had been used in Example 20 was recovered and then calcined in air at 500° C. for 16 hours then cooled to 400° C. in Nitrogen. Hydrogen was passed over the catalyst at 2.5 liters per hour, as measured at atmospheric pressure, and the pressure in the reactor was raised to 20 bar. After 1 hour the temperature was reduced to 323° C. A mixture of toluene and methanol, in the mole ratio of 3 to 1 was added to the hydrogen stream at a rate of 2.5 ml liquid per hour. The temperature was raised in steps to 460° C. The compositions of the aromatics in the product are given in Table 14.

EXAMPLE 23

Methylation of Toluene at Atmospheric Pressure in the Absence of Hydrogen

A portion of the material from Example 5 was pelleted, broken down and sieved to give aggregates of between 425 and 1000 microns. 0.5 g of this material were placed in a 5 mm internal diameter stainless steel tubular reactor and calcined at 500° C. in air at atmospheric pressure for 16 hours. The aggregates were cooled in nitrogen to 300° C. A mixture of toluene and methanol, in the mole ratio of 3 to 1, was pumped through the reactor at various flow rates. The composition of the aromatics in the product at various times can be seen in Table 15.

These Examples illustrate the use of zeolite NU-87 as a catalyst in the alkylation of toluene with methanol, both in the presence and absence of hydrogen.

EXAMPLE 24

Ethylation of Benzene

A portion of the product from Example 16 was pelleted, broken down and sieved to give a 425-1000 micron size fraction. 1.0 g of this material was placed in a stainless steel reactor tube (internal diameter 4 mm) and heated in air at 500° C. for 16 hours. The tube was then purged with nitrogen as it was cooled to 400° C.

Ethylene was passed into the tube and the pressure was allowed to rise to 13.6 bar. The ethylene flow was set at 11.2 ml/min measured at atmospheric pressure and ambient temperature. Benzene was introduced at a liquid rate of 12.5 ml/hr. The rates were then adjusted to 6.3 ml/min of ethylene and 3.2 ml/hr of benzene. The mole ratio of benzene to ethylene was then 2.25.

The compositions of the product in weight percent at various times are given in Table 16. It is clear from the results that overall selectivity to ethylbenzenes is high. Thus, zeolite NU-87 is a highly selective catalyst for the ethylation of benzene.

EXAMPLE 25

Use of NU-87 as an Etherification Catalyst

A portion of the material from Example 15 was pelleted, broken down and sieved to give a 500 to 1000 micron size fraction. 0.75 g of this material was placed in a reactor consisting of 5 stainless steel tubes (internal diameter of 5 mm) in series.

A liquid feed comprising methanol and a mixture containing mainly $C_5$ hydrocarbons of which approximately 21% by weight was 2 MB (2MB=mixture of 2-methylbutene-1 and 2-methylbutene-2) (mole ratio of 2MB to methanol of 1.0:0.7) was continuously passed through the reactor at various rates and temperatures as shown below. A pressure of 7 bar nitrogen was applied to keep the feed in the liquid state.

| Run No | Temp °C. | Total Feed Flow Rate g hour$^{-1}$ | TAME weight % in product |
|---|---|---|---|
| 1 | 50 | 27 | 0.3 |
| 2 | 70 | 11 | 1.0 |
| 3 | 70 | 7 | 1.1 |
| 4 | 95 | 11 | 3.0 |

Under these conditions no dimers of the $C_5$ hydrocarbons or dimethyl ether were produced.

This example demonstrates that NU-87 can act as a catalyst for the reaction of substituted olefins with methanol to produce ethers.

EXAMPLE 26

Propane Aromatisation 2.61 g of the material from Example 16 was refluxed with 7.2 ml of a 0.1M solution of $Ga(NO_3)_3$ diluted with 70 ml of deionised water, for 26 hours. Water was removed by rotary evaporation. The resulting powder was pelleted, broken down and sieved to give a 500 to 1000 micron size fraction. This fraction was then calcined in a tube furnace, under a stream of dry air (at a rate of 7 dm$^3$ per hour) at 530° C. for 10 hours). The resultant catalyst was analysed by AAS and found to contain 1.97% by weight gallium.

0.934 g of the catalyst was transferred to a stainless steel reactor (internal diameter of 4.6 mm) and supported on glass wool and glass balls. The catalyst bed was dehydrated for 1 hour at 530° C. under a stream of nitrogen.

A feed of pure propane gas was passed over the catalyst bed at a feed flow rate of 0.778 dm$^3$ per hour and a weight hourly space velocity of 1.53 hr$^{-1}$. The catalyst bed was maintained at 530° C. and atmospheric pressure, and the resulting gaseous products were analysed by gas chromatography. A gas analysis, after the catalyst had been on line at the reaction temperature for 30 minutes, showed that 34% of the propane feed was being converted. The concentration of benzene in the gaseous hydrocarbon products was 14.4 wt %, the concentration of toluene was 17.6 wt %, and the corresponding total concentration of xylene isomers was 6.2 wt %. Therefore, the total concentration of aromatics in the gaseous hydrocarbon products was 38.1 wt %.

This example demonstrates illustrates the use of a gallium impregnated zeolite NU-87 in the aromatisation of propane.

EXAMPLE 27

Preparation of Amines

A portion of the material from Example 16 was pelleted, broken down and sieved to give a 500-1000 micron size fraction. A sample of this material (3.42 g) was charged to a tubular stainless steel microreactor and heated to 300° C. under a flow of nitrogen before the reactant gases were introduced. The feed consisted of a gaseous mixture of ammonia and methanol and conditions were adjusted to give the desired methanol conversion. The reaction products were measured by on-line gas chromatography and found to consist of a mixture of mono-, di-and tri-methylamines. At a temperature of 350° C. using a feed containing a molar ratio of ammonia to methanol of 2.25 at a gas hourly space velocity (GHSV) of 1450 hr$^{-1}$ the methanol conversion was 98% and the product consisted of 45 mole % monomethylamine, 27 mole % dimethylamine and 28 mole % trimethylamine. At the same temperature using a molar ratio of ammonia of methanol of 2.6 at GHSV 1480 hr$^{-1}$, the methanol conversion was 99% and the product composition 48 mole % monomethylamine, 26 mole % dimethylamine and 26 mole % trimethylamine.

This example demonstrates the use of zeolite NU-87 as a catalyst for the preparation of amines.

EXAMPLE 28

Fluid Catalytic Cracking Additive

Zeolite NU-87 was evaluated as a fluid catalytic cracking (FCC) additive by adding it in small quantities to a base FCC catalyst and then monitoring its effect on the cracking products in a microactivity test (MAT) run.

Base Catalyst

The base FCC catalyst used was Resoc-1, E-Cat (Grace Davidson). The "E-Cat" indicates that the catalyst has been deactivated on line in a FCC plant. The base catalyst was decoked by calcining in air for 24 hours at 550° C. Resoc-1 is a rare earth exchanged Ultrastabilised Y zeolite based catalyst in spray dried form.

Additive Catalyst

Each sample of NU-87 was tested by preparing two catalysts.
(a) Resoc-1, E-Cat+1% by weight fresh NU-87 based on the weight of Resoc-1, E-Cat
(b) Resoc-1, E-Cat+2% by weight fresh NU-87 based on the weight of Resoc-1, E-Cat
(the % weight of NU-87 are based on anhydrous material).

Individual catalysts were prepared by thorough physical mixing of the base catalyst with a portion of material from Example 2. The mixture was then compressed. The resulting pellet was broken up and sieved to give granules with a size in the range of 44 to 70 microns.

The feedstock used in these experiments was Cincinnati gas oil. The properties of this material are as follows.

| Vacuum Distillation | °C. | |
|---|---|---|
| 10% at 760 mm | 312.7 | (595° F.) |
| 30% | 362.8 | (685° F.) |
| 50% | 407.2 | (765° F.) |
| 70% | 451.7 | (845° F.) |
| 80% | 501.1 | (934° F.) |

The MAT runs were carried out in a fixed bed unit using a 3 ml charge of Cincinnati gas oil. The weight hourly space velocity (WHSV) of individual runs is given in Table 17.

The catalyst samples had all been calcined in air at 538° C. for 1 hour before testing. The starting temperature for each run was 515.6° C.

The products were analysed by gas chromatography capillary column analysis from which the research octane number (RON) of the resulting gasoline could be determined. Table 17 lists this data.

From results given in Table 17 it can be seen that the addition of zeolite NU-87 increases the RON of gasoline. It also increases the yield of $C_3$ and $C_4$ paraffins and olefins.

EXAMPLE 29

Dewaxing of a Feedstock

A portion of the material from Example 14 was activated in a manner similar to that described in Example 15. Analysis for Na, Si and Al by AAS gave the following molar composition:

$$37.1\ SiO_2\text{---}Al_2O_3\text{---less than } 0.003 Na_2O$$

A 24.6 gram sample of this activated material was added to 200 ml of a 1M solution of nickel nitrate in deionised water. The resulting slurry was heated at 90° C. for 3.5 hours. The nickel nitrate solution was then separated by centrifuging and the zeolite powder subsequently dried at 90° C.

The zeolite powder was then nickel exchanged a second time using a fresh portion of the nickel nitrate solution. This gave nickel exchanged zeolite product A.

This procedure was repeated with a second 20.5 g sample of the activated material. This gave nickel exchanged zeolite product B. Products A and B were combined and calcined in static air as follows:
(a) temperature increasing from 25° to 150° C. over a period of 1 hour;
(b) 150° C. for 1 hour;
(c) temperature increasing from 150° to 350° C. over a period of 1 hour;
(d) 350° C. for 1 hour;
(e) temperature increasing from 350° to 540° C. over a period of 2 hours; and
f) 540° C. for 16 hours.

The resulting catalyst was analysed by AAS and found to contain 1.45% by weight of nickel.

A 25 g portion of the catalyst was reduced in a flow of hydrogen at 371° C. for 2 hours and then sulphided by passing over it a flow of 2% hydrogen sulphide in hydrogen at 371° C. for 2 hours. 150 ml of the feedstock described below was then added to the catalyst in a 300 ml autoclave. The pressure was increased to 400 psig, using hydrogen, and the temperature increased to 316° C. The autoclave was maintained for 2 hours at this temperature and pressure. (The pressure was maintained using a 15 $dm^3$/hour flow of hydrogen).

The pour point of the resulting dewaxed product was found to be $-12.2°$ C. This represents a reduction of 19.4° C. in the pour point of feedstock. Thus, this example demonstrates the utility of a nickel exchanged NU-87 in dewaxing of a feedstock.

A heavy gas oil sample was used as feedstock. Its properties are as follows:

| | |
|---|---|
| Density (at 15° C., g/ml) | 0.8556 |
| Pour Point, °C. | −7.2 |
| Cloud Point, °C. | +18 |
| Sulphur, wt % | 0.16 |
| Simulated Distillation, °C. | |
| Initial Boiling point | 119 |
| 5% | 232 |
| 10% | 262 |
| 20% | 288 |
| 30% | 304 |
| 40% | 319 |
| 50% | 332 |
| 60% | 346 |
| 70% | 361 |
| 80% | 379 |
| 90% | 404 |
| 95% | 422 |
| Final Boiling Point | 458 |

TABLE 11

| Product Composition in toluene disproportionation over NU-87 | | | | | | | |
|---|---|---|---|---|---|---|---|
| Time (hr) | 2 | 5 | 10 | 25 | 50 | 100 | 150 |
| Temp (°C.) | 350 | 350 | 350 | 350 | 350 | 352 | 357 |
| C1–C4 hydrocarbons (wt %) | 0.34 | 0.20 | 0.13 | 0.09 | 0.08 | 0.07 | 0.08 |
| Benzene (wt %) | 24.04 | 23.52 | 22.82 | 22.13 | 21.41 | 20.58 | 20.93 |
| Toluene (wt %) | 45.28 | 46.83 | 48.67 | 50.58 | 51.89 | 53.67 | 53.11 |
| Ethylbenzene (wt %) | 0.37 | 0.22 | 0.14 | 0.09 | 0.08 | 0.06 | 0.07 |
| Xylenes (wt %) | 24.57 | 24.70 | 24.30 | 23.72 | 23.38 | 22.83 | 22.91 |

TABLE 11-continued

Product Composition in toluene disproportionation over NU-87

| Time (hr) | 2 | 5 | 10 | 25 | 50 | 100 | 150 |
|---|---|---|---|---|---|---|---|
| Temp (°C.) | 350 | 350 | 350 | 350 | 350 | 352 | 357 |
| C9+ Aromatic (wt %) | 5.39 | 4.52 | 3.94 | 3.38 | 3.16 | 2.77 | 2.90 |
| Conversion (wt %) | 54.72 | 53.17 | 51.33 | 49.42 | 48.11 | 46.33 | 46.89 |

TABLE 12

Hydroisomerisation of xylenes over Nu-87

| Time (hr) | (feed) | 29 | 51 | 144 | 146 | 191 | 240 |
|---|---|---|---|---|---|---|---|
| Temp (°C.) | | 400 | 450 | 450 | 480 | 480 | 480 |
| WHSV | | 43.3 | 43.3 | 43.3 | 43.3 | 43.3 | 52.8 |
| Gas (wt %) | | 0.08 | 0.13 | 0.10 | 0.20 | 0.19 | 0.17 |
| Benzene (wt %) | | 0.16 | 0.24 | 0.19 | 0.41 | 0.44 | 0.36 |
| Toluene (wt %) | 0.05 | 2.94 | 1.32 | 0.66 | 1.43 | 2.11 | 1.43 |
| Ethylbenzene (wt %) | 4.50 | 3.47 | 3.78 | 4.08 | 3.61 | 3.39 | 3.63 |
| P Xylene (wt %) | 9.38 | 19.93 | 20.44 | 20.09 | 21.88 | 21.89 | 22.13 |
| M Xylene (wt %) | 57.42 | 47.53 | 48.81 | 49.88 | 48.37 | 47.82 | 48.36 |
| O Xylene (wt %) | 28.65 | 22.55 | 24.08 | 24.45 | 22.76 | 21.98 | 22.48 |
| C9+ Aromatic (wt %) | | 3.33 | 1.18 | 0.55 | 1.34 | 2.18 | 1.45 |
| % P Xylene made | | 10.55 | 11.06 | 10.71 | 12.50 | 12.51 | 12.75 |
| % Xylenes lost | | 5.69 | 2.22 | 1.09 | 2.55 | 3.93 | 2.61 |
| % Ethylbenzene lost | | 22.90 | 15.91 | 9.24 | 19.79 | 24.65 | 19.34 |

TABLE 13

Low Pressure Isomerisation of Xylenes over Nu-87
WHSV: 36.4 hr⁻¹ Temperature: 350° C.

| | Feed (wt %) | Products at 10 hours on line (wt %) |
|---|---|---|
| Gas | | 0.06 |
| Benzene | | 0.19 |
| Toluene | 0.05 | 6.31 |
| Ethylbenzene | 4.50 | 2.95 |
| P Xylene | 9.38 | 18.68 |
| M Xylene | 57.42 | 44.35 |
| O Xylene | 28.65 | 19.90 |
| C9+ Aromatic | | 7.56 |
| % P Xylene made | | 9.28 |
| % Xylene lost | | 13.12 |
| % Ethylbenzene lost | | 34.39 |

TABLE 14

Methylation of toluene in the presence of hydrogen

| Time (hours) | 1 | 4 | 7 | 23 | 25 | 28 | 29 |
|---|---|---|---|---|---|---|---|
| Temperature (°C.) | 325 | 350 | 370 | 390 | 420 | 440 | 460 |
| Benzene (% wt) | 0.35 | 0.76 | 0.43 | 0.14 | 0.83 | 1.05 | 2.11 |
| Toluene (% wt) | 82.32 | 81.70 | 81.68 | 89.68 | 79.96 | 81.05 | 73.85 |
| P-Xylene (% wt) | 3.06 | 3.29 | 3.31 | 2.08 | 3.53 | 3.49 | 4.58 |
| M-Xylene (% wt) | 3.73 | 4.89 | 4.60 | 2.69 | 6.43 | 6.55 | 9.49 |
| O-Xylene (% wt) | 6.25 | 4.89 | 6.10 | 3.92 | 4.98 | 4.32 | 4.42 |
| C9+ Aromatic (% wt) | 4.29 | 4.48 | 3.88 | 1.48 | 4.28 | 3.54 | 5.49 |
| Tot Xylenes (% wt) | 13.03 | 13.07 | 14.01 | 8.69 | 14.94 | 14.36 | 18.49 |
| % O-Xylene in xylenes | 48.00 | 37.39 | 43.54 | 45.15 | 33.31 | 24.32 | 23.91 |

TABLE 15

Methylation of Toluene at atmospheric pressure

| Time (hours) | 1 | 4 | 23 | 29 |
|---|---|---|---|---|
| Temperature (°C.) | 300 | 300 | 300 | 335 |
| WHSV (hr⁻¹) | 34.6 | 8.7 | 8.7 | 8.7 |
| Benzene (% wt) | 0.47 | 0.31 | 0.18 | 0.64 |
| Toluene (% wt) | 83.98 | 83.64 | 91.14 | 77.67 |
| P-Xylene (% wt) | 3.01 | 3.08 | 1.92 | 3.89 |
| M-Xylene (% wt) | 3.05 | 3.02 | 1.57 | 5.21 |
| O-Xylene (% wt) | 6.42 | 6.68 | 4.13 | 7.50 |
| C9+ Aromatic (% wt) | 3.06 | 3.27 | 1.06 | 5.09 |
| Tot Xylenes (% wt) | 12.48 | 12.78 | 7.62 | 16.60 |
| % O-Xylene in Xylenes | 51.46 | 52.25 | 54.18 | 45.19 |

TABLE 16

Ethylation of Benzene

| Time (hr) | 6 | 12 | 18 | 24 |
|---|---|---|---|---|
| Ethylene (wt %) | 0.54 | 0.68 | 7.41 | 10.81 |
| Benzene (wt %) | 61.84 | 61.80 | 71.43 | 77.92 |
| Toluene (wt %) | 0.07 | 0.00 | 0.00 | 0.00 |
| Ethylbenzene (wt %) | 27.45 | 28.10 | 16.47 | 10.03 |
| Orthoxylene (wt %) | 0.16 | 0.14 | 0.07 | 0.00 |
| C9+ Aromatics (wt %) | 9.95 | 9.29 | 4.63 | 1.23 |
| % EB in Products | 72.8 | 74.9 | 77.8 | 89.1 |
| % EB in C8 Arom. | 99.4 | 99.5 | 99.6 | 99.9 |

TABLE 17

Fluid Catalytic Cracking Additive

| Catalyst | (Comparative) Resoc-1, E-CAT | a | b |
|---|---|---|---|
| WHSV (hr⁻¹) | 15.74 | 15.97 | 16.07 |
| Temperature | | | |
| Starting | 515.6° C. | 515.6° C. | 515.6° C. |
| lowest | 501.1° C. | 496.7° C. | 490° C. |
| | Wt % | Wt % | Wt % |
| Conversion | 63.23 | 62.82 | 61.78 |
| Product Yields | | | |
| Total C3's | 4.44 | 6.77 | 7.72 |
| Propane | .84 | 1.49 | 1.98 |
| Propylene | 3.60 | 5.29 | 5.74 |
| Total C4's | 8.40 | 11.84 | 12.76 |
| I-Butane | 3.45 | 5.29 | 5.72 |
| N-Butane | .67 | .94 | 1.14 |
| Total Butenes | 4.29 | 5.60 | 5.89 |
| 1-Butene | 2.01 | 2.86 | 3.15 |
| Trans-Butenes | 1.31 | 1.58 | 1.58 |
| Cis-Butenes | .96 | 1.16 | 1.16 |
| BP range C5– 430° F. Gasoline | 44.11 | 37.20 | 33.55 |
| BP range 430– 650° F. Light Cycle Gas Oil | 22.43 | 22.24 | 22.49 |
| BP range 650° F. and above Diesel Oil | 14.34 | 14.94 | 15.73 |
| FCC Gasoline + Alkylate (VOL %) | 76.83 | 77.60 | 75.31 |
| Research Octane Number (Gasoline) | 93.3 | 97.2 | 99.6 |

BP = boiling point

We claim:

1. A catalyst comprising a zeolite designated NU-87 said zeolite having a composition expressed on an anhydrous basis (in terms of mole ratios of oxide) by the formula 100 XO₂: equal to or less than 10 Y₂O₃: equal to or less than 20 R$_{2/n}$O wherein R is at least partly hydrogen, X is silicon and/or germanium, Y is one or more of aluminium, iron, gallium, boron, titanium, vanadium, zirconium, molybdenum, arsenic, antimony, chromium and manganese and having an X-ray diffraction pattern including the lines shown in Table 2.

2. A catalyst as claimed in claim 1 in which the hydrogen is partially or completely replaced by a metal.

3. A catalyst as claimed in claim 1 or claim 2 further comprising a component selected from
   (a) a binder;
   (b) a catalyst support material;
   (c) a further zeolite or a molecular sieve;
   (d) a metal; and
   (e) a further catalyst or a combination thereof.

4. A catalyst as claimed in claim 1 where X is silicon and Y is aluminium.

5. A method for preparing a catalyst as claimed in claim 2 or claim 3 comprising
   (a) impregnation of the zeolite as defined in claim 1 with a metal compound or
   (b) subjecting the zeolite as defined in claim 1 to ion-exchange with a metal ion.

* * * * *